(12) United States Patent
Cashman et al.

(10) Patent No.: US 7,041,807 B1
(45) Date of Patent: May 9, 2006

(54) ANTIBODIES TO A YYX EPITOPE OF A MAMMALIAN PRION PROTEIN

(75) Inventors: Neil R. Cashman, Toronto (CA); Eustache Paramithiotis, Boucherville (CA); Jacek Slon-Usakiewicz, Pointe-Claire (CA); Ashkan Haghighat, Montreal (CA); Marc Pinard, Montreal (CA); Trebor Lawton, Gorham, ME (US)

(73) Assignee: Caprion Pharmaceuticals, Inc., Saint Laurent (CA)

( * ) Notice: Subject to any disclaimer, the term of this patent is extended or adjusted under 35 U.S.C. 154(b) by 342 days.

(21) Appl. No.: 09/602,775

(22) Filed: Jun. 23, 2000

Related U.S. Application Data

(60) Provisional application No. 60/140,634, filed on Jun. 23, 1999.

(51) Int. Cl.
*C07K 16/00* (2006.01)

(52) U.S. Cl. .............................. 530/389.1; 424/130.1; 435/7.1; 530/388.1; 530/389.1

(58) Field of Classification Search ............ 424/130.1; 530/300, 530, 388.1, 389.1; 435/7.1
See application file for complete search history.

(56) References Cited

U.S. PATENT DOCUMENTS

| | | | |
|---|---|---|---|
| 4,806,627 A | 2/1989 | Wisniewski et al. |
| 5,597,725 A | 1/1997 | Suzuki |
| 5,639,634 A | 6/1997 | Suzuki |
| 5,643,781 A | 7/1997 | Suzuki |
| 5,646,250 A | 7/1997 | Suzuki |
| 5,663,300 A | 9/1997 | Suzuki |
| 5,679,530 A | 10/1997 | Brentani et al. |
| 5,708,143 A | 1/1998 | Suzuki |
| 5,750,361 A | 5/1998 | Prusiner et al. |
| 5,773,572 A | 6/1998 | Fishleigh et al. |
| 5,798,224 A | 8/1998 | Suzuki |
| 5,846,533 A | 12/1998 | Prusiner et al. |
| 5,891,641 A | 4/1999 | Prusiner et al. |
| 5,891,706 A | 4/1999 | Suzuki |
| 6,150,172 A | 11/2000 | Schmerr et al. |
| 6,261,790 B1 | 7/2001 | O'Rourke |
| 6,290,954 B1 | 9/2001 | Prusiner et al. |
| 6,372,214 B1 | 4/2002 | Prusiner et al. |
| 6,462,171 B1 | 10/2002 | Soto-Jara et al. |

FOREIGN PATENT DOCUMENTS

| | | |
|---|---|---|
| DE | 197 41 607 A1 | 9/1997 |
| EP | 0 861 900 A1 | 9/1998 |
| EP | 1 213 301 A2 | 12/2002 |
| SU | 1529119 A1 | 12/1989 |
| WO | WO 87/06706 | 11/1987 |
| WO | WO 92/06220 | 4/1992 |
| WO | WO 92/08731 | 5/1992 |
| WO | WO 93/11155 | 6/1993 |
| WO | WO 93/23432 | 11/1993 |
| WO | WO 94/01116 | 1/1994 |
| WO | WO 96/32128 | 10/1996 |
| WO | 96/39834 | 12/1996 |
| WO | WO 97/10505 | 3/1997 |
| WO | WO 97/16728 | 5/1997 |
| WO | WO 97/43649 | 11/1997 |
| WO | WO 97/45746 | 12/1997 |
| WO | WO 98/37210 | 8/1998 |
| WO | WO 99/15651 | 4/1999 |
| WO | WO 99/19360 | 4/1999 |
| WO | WO 99/42829 | 8/1999 |
| WO | WO 99/66956 | 12/1999 |
| WO | WO 00/78344 A1 | 12/2000 |
| WO | WO 01/00235 | 1/2001 |
| WO | WO 04/029072 A2 | 4/2004 |

OTHER PUBLICATIONS

Harlow et al., Antibodies: a laboratory manual, Cold Spring Harbor Laboratory (1988) pp. 27-28.*
Bolton et al., "Molecular Location of a Species-Specific Epitope on the Hamster Scrapie Agent Protein," *J. Virology* 65:3667-3675 (1991).
Di Martino et al., "Production and Characterization of Antibodies to Mouse Scrapie-Amyloid Protein Elicited by Non-Carrier Linked Synthetic Peptide Immunogens," *J. Molecular Recognition* 4:85-90 (1991).
Harmeyer et al., "Synthetic Peptide Vaccines Yield Monoclonal Antibodies to Cellular and Pathological Prion Proteins of Ruminants," *J. of General Virology* 79:937-945 (1998).
Korth et al., "Prion ($PrP^{Sc}$)- Specific Epitope Defined by a Monoclonal Antibody," *Nature* 390:74-77 (1997).
Schenk et al., "Immunization with Amyloid-$\beta$ Attenuates Alzheimer-Disease-Like Pathology in the PDAPP Mouse," *Nature* 400:173-177 (1999).
St. George-Hyslop et al., "Antibody Clears Senile Plaques," *Nature* 400:116-117 (1999).

(Continued)

*Primary Examiner*—Ulrike Winkler
(74) *Attorney, Agent, or Firm*—Clark & Elbing LLP

(57) ABSTRACT

In general, the invention features antibodies specific for $PrP^{Sc}$ and diagnostic, therapeutic, and decontamination uses thereof. The invention also features synthetic peptides useful as immunogens for generating antibodies specific for $PrP^{Sc}$ and therapeutic for the treatment of prion diseases.

26 Claims, 16 Drawing Sheets

OTHER PUBLICATIONS

Figure 1A:
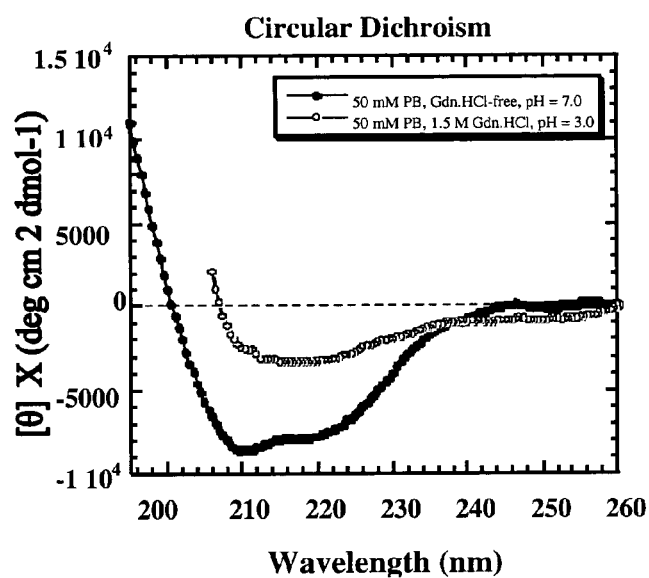

Bolton et al., "Identification of a Protein That Purifies with the Scrapie Prion," *Science* 218:1309-1311 (1982).

Brown et al., "Further studies of blood infectivity in an experimental model of transmissible spongiform encephalopathy, with an explanation of why blood components do not transmit Creutzfeldt-Jakob disease in humans," *Transfusion* 39:1169-1178 (1999).

Brown et al., "The distribution of infectivity in blood components and plasma derivatives in experimental models of transmissible spongiform encephalopathy," *Transfusion* 38:810-816 (1998).

Cioni, "Oxygen and acrylamide quenching of protein phosphorescence: correlation with protein dynamics," *Biophysical Chemistry* 87:15-24 (2000).

Cohen et al., "Pathologic Conformations of Prion Proteins," *Annu. Rev. Biochem.* 67:793-819 (1998).

Donne et al., "Structure of the recombinant full-length hamster prion protein PrP(29-231): The N terminus is highly flexible," *Proc. Natl. Acad. Sci. USA* 94:13452-13457 (1997).

Fischer et al., "Binding of disease-associated prion protein to plasminogen," *Nature* 408:479-483 (2000).

Hornemann et al., "A scrapie-like unfolding intermediate of the prion protein domain PrP(121-232) induced by acidic pH," *Proc. Natl. Acad. Sci. USA* 95:6010-6014 (1998).

Jackson et al., "Reversible Conversion of Monomeric Human Prion Protein Between Native and Fibrilogenic Conformations," *Science* 283:1935-1937 (1999).

Kascsak et al., "Mouse Polyclonal and Monoclonal Antibody to Scrapie-Associated Fibril Proteins," *Journal of Virology* 61:3688-3692 (1987).

Korth et al., "Monoclonal Antibodies Specific for the Native, Disease-Associated Isoform of the Prion Protein," *Methods in Enzymology* 309:106-122 (1999).

Korth et al., "Prion ($PrP^{Sc}$)-specific epitope defined by a monoclonal antibody," *Nature* 390:74-77 (1997).

Kondejewski et al., "Dissociation of Antimicrobial and Hemolytic Activities in Cyclic Peptide Diastereomers by Systematic Alterations in Amphipathicity," *J. Biol. Chem.* 274:13181-13192 (1999).

McGaughey et al., "π-Stacking Interactions. Alive and Well in Proteins," *J. Biol. Chem.* 273:15458-15463 (1998).

Pan et al., "Conversion of α-helices into β-sheets features in the formation of the scrapie prion proteins,"*Proc. Natl. Acad. Sci. USA* 90:10962-10966 (1993).

Pergami et al., "Semipreparative Chromatographic Method to Purify the Normal Cellular Isoform of the Prion Protein in Nondenatured Form," *Analytical Biochemistry* 236:63-73 (1996).

Prusiner "Novel Proteinaceous Infectious Particles Cause Scrapie," *Science* 216:136-144 (1982).

Prusiner "Prions," *Proc. Natl. Acad. Sci. USA* 95:13363-13383 (1998).

Riek et al., "NMR structure of the mouse prion protein domain PrP(121-231)," *Nature* 382:180-182 (1996).

Safar et al., "Eight prion strains have $PrP^{Sc}$ molecules with different conformations," *Nature Medicine* 4:1157-1165 (1998).

Swietnicki et al., "pH-dependent Stability and Conformation of the Recombinant Human Prion Protein PrP(90-231)," *Journal of Biological Chemistry* 272:27517-27520 (1997).

Williamson et al., "Mapping the Prion Protein Using Recombinant Antibodies," *Journal of Virology* 72:9413-9418 (1998).

Zahn et al., "NMR solution structure of the prion protein," *Proc. Natl. Acad. Sci. USA* 97:145-150 (2000).

Fischer et al., "Prion Protein (PrP) with Amino-Proximal Deletions Restoring Susceptibility of PrP Knockout Mice to Scrapie", *EMBO Journal.* 15:1255-1264 (1996).

Heppner et al., "Prevention of Scrapie Pathogenesis by Transgenic Expression of Anti-Prion Protein Antibodies", *Science,* 294:178-82 (2001).

Maissen et al., "Plasminogen Binds to Disease-Associated Prion Protein of Multiple Species", *Lancet,* 357:2026-2028 (2001).

Paramithiotis et al., "A Prion Protein Epitope Selective for the Pathologically Misfolded Conformation", *Nature Medicine,* 9:893-899 (2003). (Advance Online Publication).

Bacon and Anderson, "Multiple Sequence Alignment,"*J. Mol. Biol.* 191:153-161 (1986).

Bennett et al., "3D Domain Swapping: A Mechanism for Oligomer Assembly," *Protein Science* 4:2455-2648 (1995).

Bolton and Bendheim, "A Modified Host Protein Model of Scrapie," *Ciba Found. Symp.* 135:164-181 (1988).

Bradley, "BSE Transmission Studies with Particular Reference to Blood," *Dev. Biol. Stand.* 99:35-40 (1999).

Brown et al., "Iatrogenic Creutzfeldt-Jakob Disease at the Millennium," *Neurology* 55:1075-1081 (2000).

Büeler et al., "Mice Devoid of PrP are Resistant to Scrapie," *Cell* 73:1339-1347 (1993).

Büeler et al., "Normal Development and Behaviour of Mice Lacking the Neuronal Cell-Surface PrP Protein," *Nature* 356:577-582 (1992).

Cashman, "A Prion Primer," *CMAJ* 157:1381-1385 (1997).

Cashman et al., "A Prion-Specific Immunological Epitope," *Society for Neuroscience Abstracts* 27:1743 (2001).

Cashman et al., "Cellular Isoform of the Scrapie Agent Protein Participates in Lymphocyte Activation," *Cell* 61:185-192 (1990).

Caughey et al., "Binding of the Protease-Sensitive Form of Prion Protein PrP to Sulfated Glycosaminoglycan and Congo Red," *J. Virol* 68: 2135-2141 (1994).

Caughey, "Probing for Prions: Recognizing Misfolded PrP," *Nature Medicine* 9:819-820 (2003).

Chandler, "Encephalopathy in Mice Produced by Inoculation with Scrapie Brain Material," *Lancet* 6:1378-1379 (1961).

Collinge et al., "Prion Protein is Necessary for Normal Synaptic Function," *Nature* 370:295-297 (1994).

Collinge, "Variant Creutzfeldt-Jakob Disease," *Lancet* 354:317-323 (1999).

Come et al., "A Kinetic Model for Amyloid Formation in the Prion Diseases: Importance of Seeding," *Proc. Natl. Acad. Sci. USA* 90: 5959-5963 (1993).

Coulthart and Cashman, "Variant Creutzfeldt-Jakob Disease: A Summary of Current Scientific Knowledge in Relation to Pubilc Health," *CMAJ* 165:51-58 (2001).

Dayhoff et al., "A Model of Evolutionary Change in Proteins," *Atlas Protein Sequence and Structure* 5:345-352 (1978).

Eklund et al., "Pathogenesis of Scrapie Virus Infection in the Mouse," *J. Infectious Disease* 117:15-22 (1967).

Endo et al., "Diversity of Oligosaccharide Structures Linked to Asparagines of the Scrapie Prion Protein," *Biochem.* 28:8380-8388 (1989).

Engelman et al., "Identifying Nonpolar Transbilayer Helices in Amino Acid Sequences of Membrane Proteins," *Annu. Rev. Biophys. Chem.* 15:321-353 (1986).

Field, "Slow Virus Infecions of the Nervous System," *Brit. J. Exp. Path.* 8:129-239 (1969).

Fisher, "Vaccine in Mice Offers Hope in Fight Against Alzheimer's," *The New York Times, National*, pg. A16, Jul. 8, (1999).

Gorochov et al., "Properties of a Disease Specific Prion Probe," *Nature Medicine* 10:11 (2004).

Horiuchi et al., "Inhibition of Interactions and Interconversions of Prion Protein Isoforms by Peptide Fragments from the C-terminal Folded Domain," *J. Biol. Chem.* 276: 15489-15497 (2001).

Houston et al., "Influence of Preformed $\alpha$-helix and $\alpha$-helix Induction of the Activity of Cationic Antimicrobial Peptides," *J. Peptide Res.* 52:81-88 (1998).

Houston et al., "Transmission of BSE by Blood Transfusion in Sheep," *Lancet* 356: 999-1000 (2000).

Kyte and Doolittle, "A Simple Method for Displaying the Hydropathic Character of a Protein," *J. Mol. Biol.* 157:105-132 (1982).

Li et al., "The Expression and Potential Function of Cellular Prion Protein in Human Lymphocytes," *Cell. Immunol.* 207:49-58 (2001).

McKinley et al., "A Protease-Resistant Protein Is a Structural Component of the Scrapie Prion," *Cell* 35:57-62 (1983).

Merrifield, "Solid Phase Peptide Synthesis. I. The Synthesis of a Tetrapeptide," *J. Am. Chem. Soc.* 85:2149-2154 (1963).

Moore et al., "Ataxia in Prion Protein (PrP)-Deficient Mice is Associated with Upregulation of the Novel PrP-Like Protein Doppel," *J. Mol. Biol.* 292:797-817 (1999).

Morel et al., "Selective and Efficient Immunoprecipitation of the Disease-Associated Form of the Prion Protein can be Mediated by Nonspecific Interactions between Monoclonal Antibodies and Scrapie-Associated Fibrils," *J. Biol Chem.* 279: 30143-30149 (2004).

Morignat et al., "Targeted Surveillance to Assess the Prevalence of BSE in High-Risk Populations in Western France and the Associated Risk Factors," *Veterinary Record* 151:73-77 (2002).

Oesch et al., "Application of Prionics Western Blotting Procedure to Screen for BSA in Cattle Regularly Slaughtered at Swiss Abattoirs," *Arch. Virol. Supp.* 16:189-195 (2000).

Oesch et al., "A Cellular Gene Encodes Scrapie PrP 27-30 Protein," *Cell* 40:735-746 (1985).

O'Rourke et al., "Preclinical Detection of PrP$^{Sc}$ in Nictitating Membrane Lymphoid Tissue of Sheep," *Veterinary Record* 142:489-491 (1998).

Paramithiotis et al., "Properties of a Disease Specific Prion Probe, Reply," *Nature Medicine* 10:11-12 (2004).

Pattison, "The Emergence of Bovine Spongiform Encephalopathy and Related Diseases," *Emerg Infect Dis* 4:390-394 (1998).

Prusiner, "Molecular Biology of Prion Diseases," *Science* 252:1515-1522 (1991).

Prusiner et al., "Ablation of the Prion Protein (PrP) Gene in Mice Prevents Scrapie and Facilitates Production of Anti-PrP Antibodies," *Proc. Natl. Acad. Sci., USA* 90:10608-10612 (1993).

Prusiner et al., "Further Purification and Characterization of Scrapie Prions," *Biochem.* 21:6942-6950 (1982).

Ricketts et al., "Is Creutzfeldt-Jakob Disease Transmitted in Blood," *Emerg Infect Dis* 3:155-163 (1997).

Schaller et al., "Validation of a Western Immunoblotting Procedure for Bovine PrP$^{Sc}$ Detection and Its Use as a Rapid Surveillance Method for the Diagnosis of Bovine Spongiform Encephatopathy (BSE)," *Acta Neuropathol.* 98: 437-443 (1999).

Shyng et al., "Sulfated Glycans Stimulate Endocytosis of the Cellular Isoform of the Prion Protein, PrPc, in Cultured Cells," *Journal of Biological Chemistry* 270:30221-30229 (1995).

St. George-Hyslop et al., "Antibody Clears Senile Plaques," *Nature* 400:116-117 (1999).

Tam, "Recent Advances in Multiple Antigen Peptides," *J. Immunol. Methods* 198:17-32 (1996).

Tam, "Synthetic Peptide Vaccine Design: Synthesis and Properties of a High-Density Multiple Antigenic Peptide System," *Proc Natl. Acad. Sci., USA* 65: 5409-5413 (1988).

Tam and Zavala, "Multiple Antigen Peptide," *J. Immunol. Methods* 124:53-61 (1989).

Tam et al., "Membranolytic Selectivity of Cystine-Stabilized Cyclic Protegrins," *Eur. J. Biochem.* 267:3289-3300 (2000).

Taylor et al., "Infectivity in the Blood of Mice with a BSE-Derived Agent," *J. Hosp. Infect.* 46:78-79 (2000).

Tobler et al., "Sleep and Sleep Regulation in Normal and Prion Protein-Deficient Mice," *J. Neuroscience* 17:1869-1879 (1997).

Vorberg et al., "A Novel Epitope for the Specific Detection of Exogenous Prion Proteins in Transgenic Mice and Transfected Murine Cell Lines," *Virology* 255:26-31 (1999).

Will et al., "A New Variant of Creutzfeldt-Jakob Disease in the UK," *Lancet* 347:921-925 (1996).

Bendheim et al., "Antibodies to a Scrapie Prion Protein," *Nature* 310:418-421 (1984).

Cheng et al., "Identification and Cloning of ELF-1, a Developmentally Expressed Ligand for the Mek4 and Sek Receptor Tyrosine Kinases," *Cell* 79:157-168 (1994).

Demart et al., "New Insight into Abnormal Prion Protein Using Monoclonal Antibodies," *Biochem. Biophys. Res. Commun.* 265:652-657 (1999).

Dodelet et al., "Construction and Use of a Prion Protein-Alkaline Phosphatase Fusion Protein for Prion Ligand Detection," *Cold Spring Harbor Laboratory, 61$^{st}$ Symposium:Function & Dysfunction in the Nervous System*, May 29, (1996).

Fields et al., "The Two-hybrid System: an Assay for Protein-Protein Interactions," *Trends Genet.* 10:286-292 (1994).

Flanagan et al., "The kit Ligand: A Cell Surface Molecule Altered in Steel Mutant Fibroblasts," *Cell* 63:185-194 (1990).

Gomi et al., "Mice Devoid of the Glial Fibrillary Acidic Protein Develop Normally and Are Susceptible to Scrapie Prions," *Neuron* 14:29-41 (1995).

Krasemann et al., "Generation of Monoclonal Antibodies Against Human Prion Proteins in PrP0/0 Mice," *Mol. Med.* 2:725-734 (1996).

Krasermann et al., "Induction of Antibodies Against Human Prion Proteins (PrP) by DNA-mediated Immunization of PrP0/0 Mice," *J. Immunol. Methods* 199:109-118 (1996).

Krasemann et al., "Generation of Monoclonal Antibodies Against Prion Proteins with an Unconventional Nucleic Acid-based Immunization Strategy," *J. Biotechnol.* 73:119-129 (1999).

Kretzschmar et al., "Molecular Cloning of a Human Prion Protein cDNA", *DNA* 5:315-324 (1986).

Kurschner et al., "Analysis of Interaction Sites in Homo- and Heteromeric Complexes Containing Bcl-2 Family Members and the Cellular Prion Protein," *Mol. Brain Res.* 37:249-58. (1996).

Kurschner et al., "The Cellular Prion Protein (PrP) Selctively Binds to Bcl-2 in the Yeast Two-hybrid System," *Mol. Brain Res.* 30:165-168 (1995).

Mabbott et al., "T-lymphocyte Activation and the Cellular Form of the Prion Protein," *Immunology* 92:161-165 (1997).

Meggio et al., "Bovine Prion Protein as a Modulator of Protein Kinase CK2," *Biochem. J.* 352:191-196 (2000).

Morel et al., "Selective and Efficient Immunoprecipitation of the Disease-Associated Form of the Prion Protein can be Mediated by Nonspecific Interactions between Monoclonal Antibodies and Scrapie-Associated Fibrils," *J. Biol. Chem.* 279:30143-30149 (2004).

Oesch "Characterization of PrP binding proteins," *Philos. Trans. R. Soc. Lond. B Biol. Sci.* 343:443-445 (1994).

Oesch et al., "Interaction of the Prion Protein with Cellular Proteins," *Chemical Abstract* 122:49358 CA (1992).

Oesch et al., "Identification of Cellular Proteins Binding to the Scraple Prion Protein," *Biochem.* 29:5848-5855 (1990).

Priola et al., "Prion Protein and the Scrapie Agent: In Vitro Studies in Infected Neuroblastoma Cells," *Infect. Agents Dis.* 3:54-58 (1994).

Sano et al., "Protocadherins: A Large Family of Cadherin-Related Molecules in Central Nervous System,"*EMBO J.* 12:2249-2256 (1993).

Serbec et al., "Monoclonal Antibody against a Peptide of Human Prion Protein Discriminates between Creutzfeldt-Jacob's Disease-affected and Normal Brain Tissue," *J. Biol. Chem.* 279:3694-3698 (2004).

Shapiro et al., "Structural Basis of Cell-Cell Adhesion by Cadherins," *Nature* 374:327-337 (1995).

Tatzelt et al., "Scrapie in Mice Deficient in Apolipoprotein E or Glial Fibrillary Acidic Protein," *Neurology* 47:449-453 (1996).

Telling et al., "Prion Propagation in Mice Expressing Human and Chimeric PrP Transgenes Implicates the Interaction of Cellular PrP with Another Protein", *Cell* 83:79-90 (1995).

Weiss et al., "Overexpression of Active Syrian Golden Hamster Prion Protein $PrP^c$ as a Glutathione S-Transferase Fusion in Heterologous Systems," *J. Virol.* 69:4776-4783 (1995).

Westaway et al., "Degeneration of Skeletal Muscle, Peripheral Nerves, and the Central Nervous System in Transgenic Mice Overexpressing Wild-Type Prion Proteins," *Cell* 76:117-129 (1994).

Yehiely et al., "Identification of Candidate Proteins Binding to Prion Protein," *Neurobiol. Dis.* 3:339-355 (1997).

Zou et al., "Acidic pH and Detergents Enhance In Vitro Conversion of Human Brain $PrP^c$ to a $PrP^{sc}$-like Form," *J. Biol. Chem.* 277:43942-43947 (2002).

Zou et al., "Antibody to DNA Detects Scrapie but not Normal Prion Protein," *Proc. Natl. Acad. Sci. U.S.A.* 3:1380-1385 (2004).

ANASPEC On-Line Catalogue

Arrou et al., "Enantioselective Separation of Basic Amino Acids on Talc," J. Chem. Tech. Biotechnol. 63:92-96 (1995).

Chadha et al., "Heparin Binding Sites on Prions," IJBC 2:211-223 (1997).

Lindon et al., "TI Separation and Characterization of Components of Peptide Libraries," Abstract, Magn., Reson. Chem. 33:857-863 (1995).

Steiner, "Structual Evidence for the Aromatic- (i+1) Amine Hydrogen Bond in Peptides: L-Tyr-L-Tyr-L-Leu Monohydrate," Abstract, Acta Cryst. D54:584-588 (1998).

* cited by examiner

Figure 2

```
BOVINE    1    M V K S H I G S W I L V L F V A M W S D V G L C K K R P K P G G G W N T G G S R Y P G Q G S P G G N R Y P P Q G G G G W
MAN       1    - - M A N L G C W M L V L F V A T W S D L G L C K K R P K P G G - W N T G G S R Y P G Q G S P G G N R Y P P Q G G G G W
SHEEP     1    M V K S H I G S W I L V L F V A M W S D V G L C K K R P K P G G G W N T G G S R Y P G Q G S P G G N R Y P P Q G G G G W
MOUSE     1    - - M A N L G Y W L L A L F V T M W T D V G L C K K R P K P G G - W N T G G S R Y P G Q G S P G G N R Y P P Q G G - T W
HAMSTER   1    - - M A N L S Y W L L A L P V A M W T D V G L C K K R P K P G G - W N T G G S R Y P G Q G S P G G N R Y P P Q G G G T W

BOVINE    61   G Q P H G G G W G Q P H G G G W G Q P H G G G W G Q P H G G G - W G Q P H G G G W G Q G G T H G Q W N K P S K P K T N
MAN       58   G Q P H G G G W G Q P H G G G W G Q P H G G G W G Q P H G G G - W G Q - - G G G - - - - - - T H S Q W N K P S K P K T N
SHEEP     61   G Q P H G G G W G Q P H G G G W G Q P H G G G W G Q P H G G G G W G Q - - G G - - - - - - - S H S Q W N K P S K P K T N
MOUSE     57   G Q P H G G G W G Q P H G G G W G Q P H G G G W G Q P H G G G - W G Q - - G G G - - - - - - T H N Q W N K P S K P K T N
HAMSTER   58   G Q P H G G G W G Q P H G G G W G Q P H G G G W G Q P H G G G - W G Q - - G G G - - - - - - T H N Q W N K P S K P K T N

BOVINE    120  M K H V A G A A A A G A V V G G L G G Y M L G S A M S R P L I H F G S D Y E D R Y Y R E N M H R Y P N Q V Y Y R P V D Q
MAN       109  M K H M A G A A A A G A V V G G L G G Y M L G S A M S R P I I H F G S D Y E D R Y Y R E N M H R Y P N Q V Y Y R P M D E
SHEEP     112  M K H V A G A A A A G A V V G G L G G Y M L G S A M S R P L I H F G N D Y E D R Y Y R E N M Y R Y P N Q V Y Y R P V D Q
MOUSE     108  L K H V A G A A A A G A V V G G I G G Y M L G S A V S R P M I H F G N D W E D R Y Y R E N M Y R Y P N Q V Y Y R P V D Q
HAMSTER   109  M K H M A G A A A A G A V V G G L G G Y M L G S A M S R P M M H F G N D W E D R Y Y R E N M N R Y P N Q V Y Y R P V D Q

BOVINE    180  Y S N Q N N F V H D C V N I T V K E H T V T T T T K G E N F T E T D I K M M E R V V E Q M C I T Q Y Q R E S Q A Y Y D -
MAN       169  Y S N Q N N F V H D C V N I T I K Q H T V T T T T K G E N F T E T D V K M M E R V V E Q M C I T Q Y E R E S Q A Y Y D -
SHEEP     172  Y S N Q N N F V H D C V N I T V K Q H T V T T T T K G E N F T E T D I K I M E R V V E Q M C I T Q Y Q R E S Q A Y Y D -
MOUSE     168  Y S N Q N N F V H D C V N I T I K Q H T V T T T T K G E N F T E T D V K M M E R V V E Q M C V T Q Y Q K E S Q A Y Y D G
HAMSTER   169  Y N N Q N N F V H D C V N I T I K Q H T V T T T T K G E N F T E T D I K I M E R V V E Q M C T T Q Y Q K E S Q A Y Y D G

BOVINE    239  - R G A S V I L F S S P P V I L L I S F L I F L I V G
MAN       228  - R G S S M V L F S S P P V I L L I S F L I F L I V G
SHEEP     231  - R G A S V I L F S S P P V I L L I S F L I F L I V G
MOUSE     228  R R S S S T V L F S S P P V I L L I S F L I F L I V G
HAMSTER   229  - R R S S A V L F S S P P V I L L I S F L I F L M V G
```

Figure 16
A
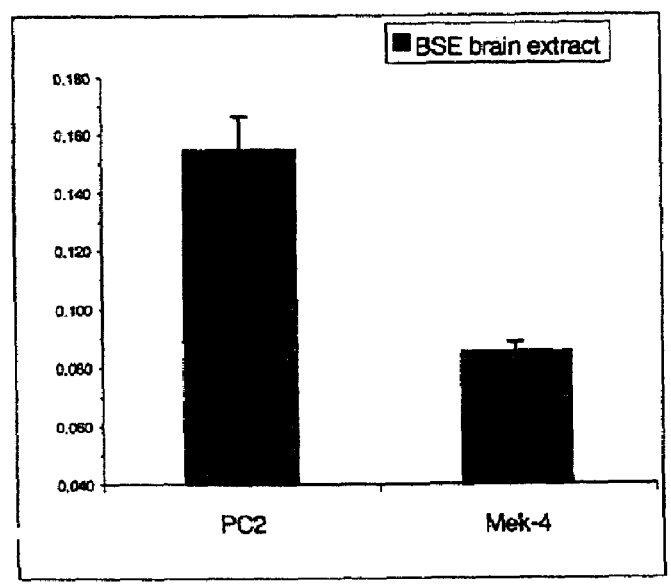
B
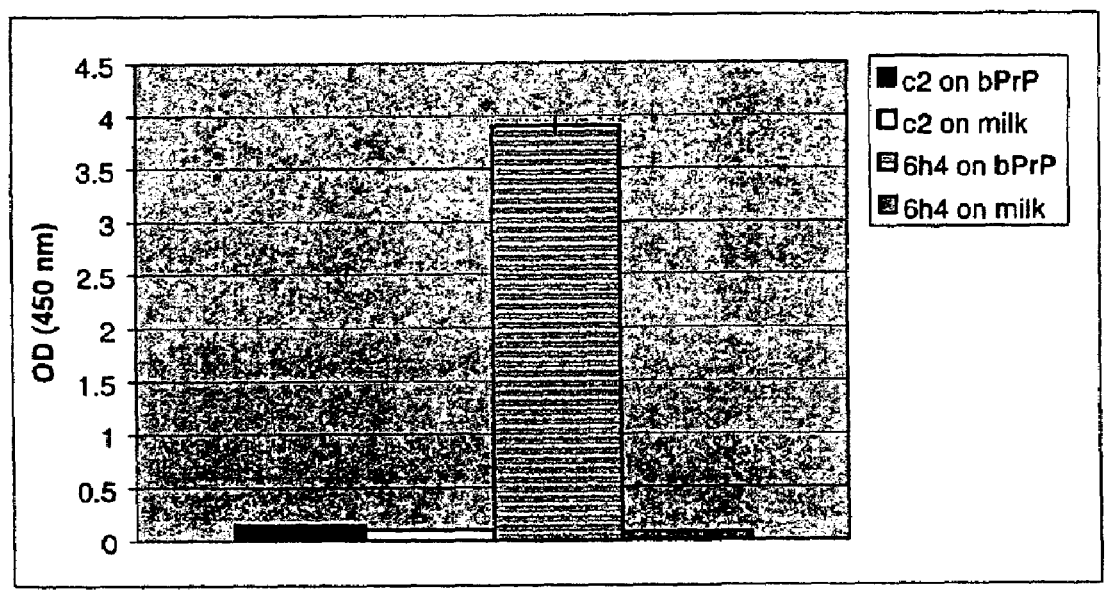

SEQUENCE LISTING

```
<160> NUMBER OF SEQ ID NOS: 34

<210> SEQ ID NO 1
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)...(4)
<223> OTHER INFORMATION: Xaa = Any Amino Acid

<400> SEQUENCE: 1

Xaa Tyr Tyr Xaa
 1

<210> SEQ ID NO 2
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)...(7)
<223> OTHER INFORMATION: Xaa = Any Amino Acid

<400> SEQUENCE: 2

Xaa Tyr Tyr Xaa Tyr Tyr Xaa
 1               5
```

```
<210> SEQ ID NO 3
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)...(10)
<223> OTHER INFORMATION: Xaa = Any Amino Acid

<400> SEQUENCE: 3

Xaa Tyr Tyr Xaa Tyr Tyr Xaa Tyr Tyr Xaa
 1               5                  10

<210> SEQ ID NO 4
<211> LENGTH: 13
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)...(13)
<223> OTHER INFORMATION: Xaa = Any Amino Acid

<400> SEQUENCE: 4

Xaa Tyr Tyr Xaa Tyr Tyr Xaa Tyr Tyr Xaa Tyr Tyr Xaa
 1               5                  10

<210> SEQ ID NO 5
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)...(16)
<223> OTHER INFORMATION: Xaa = Any Amino Acid

<400> SEQUENCE: 5

Xaa Tyr Tyr Xaa Tyr Tyr Xaa Tyr Tyr Xaa Tyr Tyr Xaa Tyr Tyr Xaa
 1               5                  10                  15

<210> SEQ ID NO 6
<211> LENGTH: 19
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)...(19)
<223> OTHER INFORMATION: Xaa = Any Amino Acid

<400> SEQUENCE: 6

Xaa Tyr Tyr Xaa Tyr Tyr Xaa Tyr Tyr Xaa Tyr Tyr Xaa Tyr Tyr Xaa
 1               5                  10                  15

Tyr Tyr Xaa

<210> SEQ ID NO 7
<211> LENGTH: 22
<212> TYPE: PRT
<213> ORGANISM: Artificial Sequence
<220> FEATURE:
<223> OTHER INFORMATION: Synthetic peptide
<220> FEATURE:
```

```
<221> NAME/KEY: VARIANT
<222> LOCATION: (1)...(22)
<223> OTHER INFORMATION: Xaa = Any Amino Acid

<400> SEQUENCE: 7

Xaa Tyr Tyr Xaa Tyr Tyr Xaa Tyr Tyr Xaa Tyr Tyr Xaa Tyr Tyr Xaa
 1               5                   10                  15

Tyr Tyr Xaa Tyr Tyr Xaa
            20

<210> SEQ ID NO 8
<211> LENGTH: 25
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)...(25)
<223> OTHER INFORMATION: Xaa = Any Amino Acid

<400> SEQUENCE: 8

Xaa Tyr Tyr Xaa Tyr Tyr Xaa Tyr Tyr Xaa Tyr Tyr Xaa Tyr Tyr Xaa
 1               5                   10                  15

Tyr Tyr Xaa Tyr Tyr Xaa Tyr Tyr Xaa
            20                  25

<210> SEQ ID NO 9
<211> LENGTH: 28
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)...(28)
<223> OTHER INFORMATION: Xaa = Any Amino Acid

<400> SEQUENCE: 9

Xaa Tyr Tyr Xaa Tyr Tyr Xaa Tyr Tyr Xaa Tyr Tyr Xaa Tyr Tyr Xaa
 1               5                   10                  15

Tyr Tyr Xaa Tyr Tyr Xaa Tyr Tyr Xaa Tyr Tyr Xaa
            20                  25

<210> SEQ ID NO 10
<211> LENGTH: 31
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)...(31)
<223> OTHER INFORMATION: Xaa = Any Amino Acid

<400> SEQUENCE: 10

Xaa Tyr Tyr Xaa Tyr Tyr Xaa Tyr Tyr Xaa Tyr Tyr Xaa Tyr Tyr Xaa
 1               5                   10                  15

Tyr Tyr Xaa Tyr Tyr Xaa Tyr Tyr Xaa Tyr Tyr Xaa Tyr Tyr Xaa
            20                  25                  30

<210> SEQ ID NO 11
<211> LENGTH: 34
<212> TYPE: PRT
<213> ORGANISM: Artificial Sequence
<220> FEATURE:
<223> OTHER INFORMATION: Synthetic peptide
```

```
<220> FEATURE:
<221> NAME/KEY: VARIANT
<222> LOCATION: (1)...(34)
<223> OTHER INFORMATION: Xaa = Any Amino Acid

<400> SEQUENCE: 11

Xaa Tyr Tyr Xaa Tyr Tyr Xaa Tyr Tyr Xaa Tyr Tyr Xaa Tyr Tyr Xaa
 1               5                  10                  15

Tyr Tyr Xaa Tyr Tyr Xaa Tyr Tyr Xaa Tyr Tyr Xaa Tyr Tyr Xaa Tyr
            20                  25                  30

Tyr Xaa

<210> SEQ ID NO 12
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)...(4)
<223> OTHER INFORMATION: Xaa = Any Amino Acid

<400> SEQUENCE: 12

Xaa Tyr Tyr Arg
 1

<210> SEQ ID NO 13
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)...(4)
<223> OTHER INFORMATION: Xaa = Any Amino Acid

<400> SEQUENCE: 13

Xaa Tyr Tyr Gln
 1

<210> SEQ ID NO 14
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)...(4)
<223> OTHER INFORMATION: Xaa = Any Amino Acid

<400> SEQUENCE: 14

Xaa Tyr Tyr Asp
 1

<210> SEQ ID NO 15
<211> LENGTH: 13
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)...(13)
<223> OTHER INFORMATION: Xaa = Any Amino Acid

<400> SEQUENCE: 15
```

Xaa Tyr Tyr Xaa Xaa Tyr Tyr Xaa Tyr Tyr Tyr Xaa
1               5                   10

<210> SEQ ID NO 16
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)...(16)
<223> OTHER INFORMATION: Xaa = Any Amino Acid

<400> SEQUENCE: 16

Xaa Tyr Tyr Xaa Xaa Tyr Tyr Xaa Tyr Tyr Tyr Xaa Tyr Tyr Xaa
1               5                   10                  15

<210> SEQ ID NO 17
<211> LENGTH: 19
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)...(19)
<223> OTHER INFORMATION: Xaa = Any Amino Acid

<400> SEQUENCE: 17

Xaa Tyr Tyr Xaa Xaa Tyr Tyr Xaa Tyr Tyr Tyr Xaa Tyr Tyr Xaa
1               5                   10                  15

Tyr Tyr Xaa

<210> SEQ ID NO 18
<211> LENGTH: 22
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)...(22)
<223> OTHER INFORMATION: Xaa = Any Amino Acid

<400> SEQUENCE: 18

Xaa Tyr Tyr Xaa Xaa Tyr Tyr Xaa Tyr Tyr Tyr Xaa Tyr Tyr Xaa
1               5                   10                  15

Tyr Tyr Xaa Tyr Tyr Xaa
            20

<210> SEQ ID NO 19
<211> LENGTH: 25
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)...(25)
<223> OTHER INFORMATION: Xaa = Any Amino Acid

<400> SEQUENCE: 19

Xaa Tyr Tyr Xaa Xaa Tyr Tyr Xaa Tyr Tyr Tyr Xaa Tyr Tyr Xaa
1               5                   10                  15

Tyr Tyr Xaa Tyr Tyr Xaa Tyr Tyr Xaa
            20                  25

```
<210> SEQ ID NO 20
<211> LENGTH: 28
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)...(28)
<223> OTHER INFORMATION: Xaa = Any Amino Acid

<400> SEQUENCE: 20

Xaa Tyr Tyr Xaa Xaa Tyr Tyr Xaa Tyr Tyr Tyr Tyr Xaa Tyr Tyr Xaa
 1               5                  10                  15

Tyr Tyr Xaa Tyr Tyr Xaa Tyr Tyr Xaa Tyr Tyr Xaa
            20                  25

<210> SEQ ID NO 21
<211> LENGTH: 31
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)...(31)
<223> OTHER INFORMATION: Xaa = Any Amino Acid

<400> SEQUENCE: 21

Xaa Tyr Tyr Xaa Xaa Tyr Tyr Xaa Tyr Tyr Tyr Tyr Xaa Tyr Tyr Xaa
 1               5                  10                  15

Tyr Tyr Xaa Tyr Tyr Xaa Tyr Tyr Xaa Tyr Tyr Xaa Tyr Tyr Xaa
            20                  25                  30

<210> SEQ ID NO 22
<211> LENGTH: 34
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)...(34)
<223> OTHER INFORMATION: Xaa = Any Amino Acid

<400> SEQUENCE: 22

Xaa Tyr Tyr Xaa Xaa Tyr Tyr Xaa Tyr Tyr Tyr Tyr Xaa Tyr Tyr Xaa
 1               5                  10                  15

Tyr Tyr Xaa Tyr Tyr Xaa Tyr Tyr Xaa Tyr Tyr Xaa Tyr Tyr Xaa Tyr
            20                  25                  30

Tyr Xaa

<210> SEQ ID NO 23
<211> LENGTH: 37
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)...(37)
<223> OTHER INFORMATION: Xaa = Any Amino Acid

<400> SEQUENCE: 23

Xaa Tyr Tyr Xaa Xaa Tyr Tyr Xaa Tyr Tyr Tyr Tyr Xaa Tyr Tyr Xaa
 1               5                  10                  15
```

```
Tyr Tyr Xaa Tyr Tyr Xaa Tyr Tyr Xaa Tyr Tyr Xaa Tyr
            20                  25                  30

Tyr Xaa Tyr Tyr Xaa
        35

<210> SEQ ID NO 24
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)...(40)
<223> OTHER INFORMATION: Xaa = Any Amino Acid

<400> SEQUENCE: 24

Xaa Tyr Tyr Xaa Xaa Tyr Tyr Xaa Tyr Tyr Tyr Xaa Tyr Tyr Xaa
 1               5                  10                  15

Tyr Tyr Xaa Tyr Tyr Xaa Tyr Tyr Xaa Tyr Tyr Xaa Tyr Tyr Xaa Tyr
            20                  25                  30

Tyr Xaa Tyr Xaa Tyr Tyr Xaa
        35                  40

<210> SEQ ID NO 25
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)...(10)
<223> OTHER INFORMATION: Xaa = Any Amino Acid

<400> SEQUENCE: 25

Xaa Tyr Tyr Arg Arg Tyr Tyr Arg Tyr Tyr
 1               5                  10

<210> SEQ ID NO 26
<211> LENGTH: 264
<212> TYPE: PRT
<213> ORGANISM: Bos taurus

<400> SEQUENCE: 26

Met Val Lys Ser His Ile Gly Ser Trp Ile Leu Val Leu Phe Val Ala
 1               5                  10                  15

Met Trp Ser Asp Val Gly Leu Cys Lys Lys Arg Pro Lys Pro Gly Gly
            20                  25                  30

Gly Trp Asn Thr Gly Gly Ser Arg Tyr Pro Gly Gln Gly Ser Pro Gly
        35                  40                  45

Gly Asn Arg Tyr Pro Pro Gln Gly Gly Gly Trp Gly Gln Pro His
    50                  55                  60

Gly Gly Gly Trp Gly Gln Pro His Gly Gly Trp Gly Gln Pro His
65                  70                  75                  80

Gly Gly Gly Trp Gly Gln Pro His Gly Gly Trp Gly Gln Pro His
                85                  90                  95

Gly Gly Gly Gly Trp Gly Gln Gly Gly Thr His Gly Gln Trp Asn Lys
                100                 105                 110

Pro Ser Lys Pro Lys Thr Asn Met Lys His Val Ala Gly Ala Ala Ala
            115                 120                 125
```

-continued

```
Ala Gly Ala Val Val Gly Gly Leu Gly Gly Tyr Met Leu Gly Ser Ala
            130                 135                 140

Met Ser Arg Pro Leu Ile His Phe Gly Ser Asp Tyr Glu Asp Arg Tyr
145                 150                 155                 160

Tyr Arg Glu Asn Met His Arg Tyr Pro Asn Gln Val Tyr Tyr Arg Pro
                165                 170                 175

Val Asp Gln Tyr Ser Asn Gln Asn Asn Phe Val His Asp Cys Val Asn
            180                 185                 190

Ile Thr Val Lys Glu His Thr Val Thr Thr Thr Lys Gly Glu Asn
            195                 200                 205

Phe Thr Glu Thr Asp Ile Lys Met Met Glu Arg Val Val Glu Gln Met
210                 215                 220

Cys Ile Thr Gln Tyr Gln Arg Glu Ser Gln Ala Tyr Tyr Gln Arg Gly
225                 230                 235                 240

Ala Ser Val Ile Leu Phe Ser Ser Pro Val Ile Leu Leu Ile Ser
                245                 250                 255

Phe Leu Ile Phe Leu Ile Val Gly
            260

<210> SEQ ID NO 27
<211> LENGTH: 253
<212> TYPE: PRT
<213> ORGANISM: Homo sapiens

<400> SEQUENCE: 27

Met Ala Asn Leu Gly Cys Trp Met Leu Val Leu Phe Val Ala Thr Trp
1               5                   10                  15

Ser Asp Leu Gly Leu Cys Lys Lys Arg Pro Lys Pro Gly Gly Trp Asn
            20                  25                  30

Thr Gly Gly Ser Arg Tyr Pro Gly Gln Gly Ser Pro Gly Gly Asn Arg
        35                  40                  45

Tyr Pro Pro Gln Gly Gly Gly Trp Gly Gln Pro His Gly Gly Gly
    50                  55                  60

Trp Gly Gln Pro His Gly Gly Gly Trp Gly Gln Pro His Gly Gly Gly
65                  70                  75                  80

Trp Gly Gln Pro His Gly Gly Gly Trp Gly Gln Gly Gly Gly Thr His
                85                  90                  95

Ser Gln Trp Asn Lys Pro Ser Lys Pro Lys Thr Asn Met Lys His Met
            100                 105                 110

Ala Gly Ala Ala Ala Gly Ala Val Val Gly Gly Leu Gly Gly Tyr
        115                 120                 125

Met Leu Gly Ser Ala Met Ser Arg Pro Ile Ile His Phe Gly Ser Asp
130                 135                 140

Tyr Glu Asp Arg Tyr Tyr Arg Glu Asn Met His Arg Tyr Pro Asn Gln
145                 150                 155                 160

Val Tyr Tyr Arg Pro Met Asp Glu Tyr Ser Asn Gln Asn Asn Phe Val
                165                 170                 175

His Asp Cys Val Asn Ile Thr Ile Lys Gln His Thr Val Thr Thr Thr
            180                 185                 190

Thr Lys Gly Glu Asn Phe Thr Glu Thr Asp Val Lys Met Met Glu Arg
        195                 200                 205

Val Val Glu Gln Met Cys Ile Thr Gln Tyr Glu Arg Glu Ser Gln Ala
    210                 215                 220

Tyr Tyr Gln Arg Gly Ser Ser Met Val Leu Phe Ser Ser Pro Pro Val
225                 230                 235                 240
```

```
Ile Leu Leu Ile Ser Phe Leu Ile Phe Leu Ile Val Gly
            245                 250
```

<210> SEQ ID NO 28
<211> LENGTH: 256
<212> TYPE: PRT
<213> ORGANISM: Ovis aries

<400> SEQUENCE: 28

```
Met Val Lys Ser His Ile Gly Ser Trp Ile Leu Val Leu Phe Val Ala
  1               5                  10                  15

Met Trp Ser Asp Val Gly Leu Cys Lys Lys Arg Pro Lys Pro Gly Gly
             20                  25                  30

Gly Trp Asn Thr Gly Gly Ser Arg Tyr Pro Gly Gln Gly Ser Pro Gly
         35                  40                  45

Gly Asn Arg Tyr Pro Pro Gln Gly Gly Gly Trp Gly Gln Pro His
 50                  55                  60

Gly Gly Gly Trp Gly Gln Pro His Gly Gly Gly Trp Gly Gln Pro His
 65                  70                  75                  80

Gly Gly Gly Trp Gly Gln Pro His Gly Gly Gly Trp Gly Gln Gly
                 85                  90                  95

Gly Ser His Ser Gln Trp Asn Lys Pro Ser Lys Pro Lys Thr Asn Met
            100                 105                 110

Lys His Val Ala Gly Ala Ala Ala Gly Ala Val Val Gly Gly Leu
        115                 120                 125

Gly Gly Tyr Met Leu Gly Ser Ala Met Ser Arg Pro Leu Ile His Phe
    130                 135                 140

Gly Asn Asp Tyr Glu Asp Arg Tyr Tyr Arg Glu Asn Met Tyr Arg Tyr
145                 150                 155                 160

Pro Asn Gln Val Tyr Tyr Arg Pro Val Asp Arg Tyr Ser Asn Gln Asn
                165                 170                 175

Asn Phe Val His Asp Cys Val Asn Ile Thr Val Lys Gln His Thr Val
            180                 185                 190

Thr Thr Thr Thr Lys Gly Glu Asn Phe Thr Glu Thr Asp Ile Lys Ile
        195                 200                 205

Met Glu Arg Val Val Glu Gln Met Cys Ile Thr Gln Tyr Gln Arg Glu
    210                 215                 220

Ser Gln Ala Tyr Tyr Gln Arg Gly Ala Ser Val Ile Leu Phe Ser Ser
225                 230                 235                 240

Pro Pro Val Ile Leu Leu Ile Ser Phe Leu Ile Phe Leu Ile Val Gly
                245                 250                 255
```

<210> SEQ ID NO 29
<211> LENGTH: 254
<212> TYPE: PRT
<213> ORGANISM: Mus musculus

<400> SEQUENCE: 29

```
Met Ala Asn Leu Gly Tyr Trp Leu Leu Ala Leu Phe Val Thr Met Trp
  1               5                  10                  15

Thr Asp Val Gly Leu Cys Lys Lys Arg Pro Lys Pro Gly Gly Trp Asn
             20                  25                  30

Thr Gly Gly Ser Arg Tyr Pro Gly Gln Gly Ser Pro Gly Gly Asn Arg
         35                  40                  45

Tyr Pro Pro Gln Gly Gly Thr Trp Gly Gln Pro His Gly Gly Gly Trp
     50                  55                  60
```

-continued

```
Gly Gln Pro His Gly Gly Ser Trp Gly Gln Pro His Gly Gly Ser Trp
 65                  70                  75                  80

Gly Gln Pro His Gly Gly Gly Trp Gly Gln Gly Gly Gly Thr His Asn
                 85                  90                  95

Gln Trp Asn Lys Pro Ser Lys Pro Lys Thr Asn Leu Lys His Val Ala
            100                 105                 110

Gly Ala Ala Ala Gly Ala Val Val Gly Gly Leu Gly Gly Tyr Met
        115                 120                 125

Leu Gly Ser Ala Met Ser Arg Pro Met Ile His Phe Gly Asn Asp Trp
130                 135                 140

Glu Asp Arg Tyr Tyr Arg Glu Asn Met Tyr Arg Tyr Pro Asn Gln Val
145                 150                 155                 160

Tyr Tyr Arg Pro Val Asp Gln Tyr Ser Asn Gln Asn Asn Phe Val His
                165                 170                 175

Asp Cys Val Asn Ile Thr Ile Lys Gln His Thr Val Thr Thr Thr Thr
                180                 185                 190

Lys Gly Glu Asn Phe Thr Glu Thr Asp Val Lys Met Met Glu Arg Val
            195                 200                 205

Val Glu Gln Met Cys Val Thr Gln Tyr Gln Lys Glu Ser Gln Ala Tyr
210                 215                 220

Tyr Asp Gly Arg Arg Ser Ser Thr Val Leu Phe Ser Ser Pro Pro
225                 230                 235                 240

Val Ile Leu Leu Ile Ser Phe Leu Ile Phe Leu Ile Val Gly
                245                 250
```

<210> SEQ ID NO 30
<211> LENGTH: 254
<212> TYPE: PRT
<213> ORGANISM: Mesocricetus auratus

<400> SEQUENCE: 30

```
Met Ala Asn Leu Ser Tyr Trp Leu Leu Ala Leu Phe Val Ala Met Trp
 1               5                  10                  15

Thr Asp Val Gly Leu Cys Lys Lys Arg Pro Lys Pro Gly Gly Trp Asn
                20                  25                  30

Thr Gly Gly Ser Arg Tyr Pro Gly Gln Gly Ser Pro Gly Gly Asn Arg
            35                  40                  45

Tyr Pro Pro Gln Gly Gly Gly Thr Trp Gly Gln Pro His Gly Gly Gly
        50                  55                  60

Trp Gly Gln Pro His Gly Gly Gly Trp Gly Gln Pro His Gly Gly Gly
 65                  70                  75                  80

Trp Gly Gln Pro His Gly Gly Gly Trp Gly Gln Gly Gly Gly Thr His
                 85                  90                  95

Asn Gln Trp Asn Lys Pro Ser Lys Pro Lys Thr Asn Met Lys His Met
            100                 105                 110

Ala Gly Ala Ala Ala Ala Gly Ala Val Val Gly Gly Leu Gly Gly Tyr
        115                 120                 125

Met Leu Gly Ser Ala Met Ser Arg Pro Met Met His Phe Gly Asn Asp
130                 135                 140

Trp Glu Asp Arg Tyr Tyr Arg Glu Asn Met Asn Arg Tyr Pro Asn Gln
145                 150                 155                 160

Val Tyr Tyr Arg Pro Val Asp Gln Tyr Asn Asn Gln Asn Asn Phe Val
                165                 170                 175

His Asp Cys Val Asn Ile Thr Ile Lys Gln His Thr Val Thr Thr Thr
```

```
                          180             185             190
Thr Lys Gly Glu Asn Phe Thr Glu Thr Asp Ile Lys Ile Met Glu Arg
            195             200             205
Val Val Glu Gln Met Cys Thr Thr Gln Tyr Gln Lys Glu Ser Gln Ala
            210             215             220
Tyr Tyr Asp Gly Arg Arg Ser Ser Ala Val Leu Phe Ser Ser Pro Pro
225             230             235             240
Val Ile Leu Leu Ile Ser Phe Leu Ile Phe Leu Met Val Gly
                245             250

<210> SEQ ID NO 31
<211> LENGTH: 9
<212> TYPE: PRT
<213> ORGANISM: Artificial Sequence
<220> FEATURE:
<223> OTHER INFORMATION: Synthetic peptide

<400> SEQUENCE: 31

Tyr Tyr Arg Arg Tyr Tyr Arg Tyr Tyr
1               5

<210> SEQ ID NO 32
<211> LENGTH: 4
<212> TYPE: PRT
<213> ORGANISM: Artificial Sequence
<220> FEATURE:
<223> OTHER INFORMATION: Synthetic peptide

<400> SEQUENCE: 32

Cys Tyr Tyr Arg
1

<210> SEQ ID NO 33
<211> LENGTH: 10
<212> TYPE: PRT
<213> ORGANISM: Artificial Sequence
<220> FEATURE:
<223> OTHER INFORMATION: Synthetic peptide

<400> SEQUENCE: 33

Cys Tyr Tyr Arg Arg Tyr Tyr Arg Tyr Tyr
1               5                   10

<210> SEQ ID NO 34
<211> LENGTH: 10
<212> TYPE: PRT
<213> ORGANISM: Artificial Sequence
<220> FEATURE:
<223> OTHER INFORMATION: Synthetic peptide

<400> SEQUENCE: 34

Cys Lys Tyr Glu Asp Arg Tyr Tyr Arg Glu
1               5                   10
```

ANTIBODIES TO A YYX EPITOPE OF A MAMMALIAN PRION PROTEIN

This application claims benefit of U.S. provisional application 60/140,634, filed on Jun. 23, 1999.

BACKGROUND OF THE INVENTION

This invention relates to PrP$^{Sc}$-specific antibodies and to peptides used for their generation. These antibodies are suitable for detecting PrP$^{Sc}$ in a sample, and for purifying PrP$^{Sc}$. Additionally, the invention relates to diagnostic aids for the detection of PrP$^{Sc}$, pharmaceuticals that contain or mimic PrP$^{Sc}$-specific conformational epitopes, and methods for prion decontamination.

Prions are infectious agents that are associated with neurodegenerative syndromes characterized by spongiform change (e.g., microcavitation of the brain, usually predominant in gray matter), neuronal cell loss, astrocytic proliferation disproportionate to neuronal loss, and accumulation of an abnormal amyloidogenic protein, sometimes in discrete plaques in the brain. It is possible that neurodegeneration in prion diseases shares certain underlying mechanisms with other more common neurodegenerative syndromes such as Alzheimer's Disease, amyotrophic lateral sclerosis, and Parkinson's disease.

The agents that transmit these diseases differ markedly from viruses and viroids in that no chemical or physical evidence for a nucleic acid component has been reproducibly detected in infectious materials (Prusiner, *Science,* 216: 136–144, 1982). A major step in the study of prions and the diseases that they cause was the discovery and purification of a protein designated prion protein (PrP) (Bolton et al., *Science* 218:1309–11, 1982; Prusiner et al., *Biochemistry,* 21:6942–50, 1982; McKinley et al., *Cell,* 35:57–62, 1983). When purified using proteinase K digestion, a 27–30 kD protease-resistant protein was discovered in scrapie-affected hamster brain, and was termed PrP 27–30, later found to be a fragment of PrP$^{Sc}$ (Bolton, *Science,* 218:1309–1311, 1982).

According to the prion hypothesis, prion infectivity resides in PrP$^{Sc}$. PrP$^{Sc}$ is at least strongly associated with infectivity and appears to be a reliable surrogate for prion infection. PrP$^{Sc}$ is a conformational variant of a host-encoded cellular protein designated PrP$^{C}$ (Oesch et al., *Cell,* 40:735–746, 1985), which is a glycosylphosphatidylinositol (GPI)-linked cell surface protein with a molecular mass of 33–35 kD.

PrP$^{C}$ has been isolated from normal brain, and has been found to be protease-sensitive and not associated with scrapie disease-producing activity (Bendheim et al., *Ciba Found. Symp.* 164–177, 988). According to the prion theory, PrP$^{C}$ converts into PrP$^{Sc}$ autocatalytically (Prusiner, *Proc. Natl. Acad. Sci, USA* 95:13363–83, 1998). More recently, it was reported that PrP$^{C}$ can be converted to a protease-resistant form in vitro by PrP$^{Sc}$ (Kocisko et al., *Nature,* 370:471–473, 1994). PrP$^{C}$ is an evolutionarily conserved membrane protein for which the actual biological or physiological function is unknown. Mice devoid of PrP$^{C}$ are viable and show no obvious signs of neurological and physical impairment (Bueler et al., *Nature,* 356:577–582, 1992). Additionally, these mice are not susceptible to prion infection, underscoring the central importance of PrP in the replication of infectivity (Bueler et al., *Cell,* 73:1339–1347, 1993; Prusiner et al., *Proc. Natl. Acad. Sci. USA,* 90:10608–10612, 1993). Targeted investigations of PrP knockout mice revealed impaired synaptic function (Collinge et al., *Nature,* 370:295–297, 1994) and altered sleep regulation (Tobler et al., *J. Neurosci.,* 17:1869–79). Moreover, PrP$^{C}$ has been shown to modify T cell activation induced by concanavalin A stimulation (Cashman et al., *Cell* 61:185–192, 1990), indicating a functional role for the protein.

The prion diseases are a group of rapidly progressive, fatal, and untreatable neurodegenerative syndromes. Human prion diseases include Creutzfeldt-Jakob disease (CJD), which has sporadic, iatrogenic, and familial forms; and variant CJD ("vCJD"), likely derived from the consumption of cattle tissues contaminated with the agent of bovine spongiform encephalopathy (reviewed in Cashman, *Can. Med. Assoc. J.* 157:1381–5, 1997). CJD has been accidentally transmitted between humans by contaminated cadaveric pituitary hormones, dura mater transplantation, neurosurgical instrumentation, and corneal transplantation (Brown et al., *Lancet* 340:24–7, 1992). The potential risk of transmitting CJD through blood and blood products is of worldwide concern. Moreover, scrapie in sheep and goats is a common and economically important prion-related disease in North America, as is bovine spongiform encephalopathy (BSE) in Great Britain. According to Britain's Ministry of Agriculture, Fisheries and Food, more than 4,347,380 cattle have been destroyed, because they were deemed old enough to conceivably harbor the disease agent. The Ministry of Agriculture has estimated that the total cost of the epidemic will reach $7.13 billion by 2002. More than 173,000 bovines from all over Britain have been confirmed to be infected, and hundreds of thousands more might have entered the food supply undetected.

Additionally, the United States and Canada have now implemented a blood donor deferral for individuals who resided in the UK during the early and peak years of the BSE epidemic. Such a restriction has been adopted as a precaution against the risk of transmitting a vCJD, which to date has afflicted over 60 Britons since 1996. The Canadian Blood Services estimates that 120,000 of its 600,000 active donors, or 22%, have visited Britain since 1980 (*Montreal Gazette,* May 6, 1999). Many new donors have been recruited to replace the loss, raising several concerns. One such concern is that the blood of new donors is not as safe since it has only been screened once for illnesses such as hepatitis and human immunodeficiency virus.

Accordingly, a need exists for diagnostic methods suitable for mass screening of prion infected blood or tissues. The availability of antibodies that distinguish PrP$^{C}$ from PrP$^{Sc}$ would therefore be of great value in development of a test for prion infection. Furthermore, a need exists for therapeutic agents that prevent and/or treat prion diseases.

SUMMARY OF THE INVENTION

As is discussed herein, evidence is provided demonstrating that a YYX continuous epitope of PrP is useful for generating antibodies specific for PrP$^{Sc}$. In particular, we have demonstrated that immunization protocols utilizing a short continuous synthetic peptide from the PrP sequence resulted in the generation of high-affinity polyclonal and monoclonal antibodies specific to PrP$^{Sc}$. Moreover, such antibodies were also observed to lack detectable reactivity with PrP$^{C}$. In one example, a peptide including a YYR sequence was chosen based on molecular modeling analysis of the conformational change from PrP$^{C}$ to PrP$^{Sc}$, that predicted a sequence which is solvent-accessible on the molecular surface of the PrP$^{Sc}$ isoform of the protein.

Accordingly, the invention features epitope-specific anti-PrP antibodies or fragments thereof that bind with high binding affinity to a continuous YYX epitope of a mammalian PrP$^{Sc}$. Preferably, the antibody binds to a YYR epitope; a YYQ epitope; or a YYD epitope of a mammalian PrP$^{Sc}$. In preferred embodiments, the antibody is a monoclonal or a polyclonal antibody. Such antibodies include IgG, IgM, IgE, IgD, or IgA antibodies, as well as fragments such as Fab or Fv fragments. Such anti-PrP antibodies are advantageously directed against a particular PrP$^{Sc}$ epitope. In addition, antibodies that bind to PrP$^{Sc}$ can be used to quantitate PrP$^{Sc}$ in any standard diagnostic assay.

In still another related aspect, the invention features the use of epitope-specific anti-PrP antibodies in an immunological detection procedure for the diagnosis of infective disease-specific prions. Anti-PrP antibodies that react specifically with PrP$^{Sc}$ can be prepared using an appropriately adapted PrP peptide as has been illustrated herein. The invention particularly relates to diagnostic aids that contain the PrP peptide, and/or epitope-specific anti-PrP antibodies. In addition, the invention relates to antibodies that selectively bind to disease-specific prion protein and not normal prion protein.

In another aspect, the invention features a prion protein peptide with the sequence tyrosine-tyrosine-arginine (YYR). Preferably, the peptide is a tripeptide that is linked to a carrier, making the peptide more immunogenic, allowing for the preparation of high-affinity anti-PrP antibodies. The synthesis of such a tripeptide is described herein. According to the invention, such short peptides (e.g., the YYR, YYQ, or YYD tripeptides) represent determinants that are accessible in the PrP$^{Sc}$ isoform of the prion protein, but not in the normal PrP$^{C}$ isoform, and/or are clustered in PrP$^{Sc}$ in a manner which allows antibody detection. For example, the YYR tripeptide is contained within two of the three prion protein epitopes; however, this tripeptide has not been previously identified as the specific basis of PrP$^{Sc}$ immunoreactivity. Moreover, such sequences are highly conserved across a number of species including, but not limited to bovine, man, sheep, mouse, and hamster (FIG. 2).

In still another aspect, the invention further features a synthetic peptide having the formula:

A-Tyr-Tyr-B-(Tyr-Tyr-B)$_n$ (SEQ ID NOS: 1–11)

wherein A is either any amino acid or is absent; B is either any amino acid or is absent; and n is from 0 to 10, inclusive. In preferred embodiments, at least one of A and B is not Tyr. In other preferred embodiments, A or B are chosen from Ala, Cys, Asp, Glu, Phe, Gly, His, Ile, Lys, Leu, Met, Asn, Pro, Gln, Arg, Ser, Thr, Val, or Trp. In other preferred embodiments, the peptide is linked to an immunological carrier. Such peptides include, without limitation, A-Tyr-Tyr-Arg (SEQ ID NO: 12); A-Tyr-Tyr-Gln (SEQ ID NO: 13); A-Tyr-Tyr-Asp (SEQ ID NO: 14); or any pharmaceutically acceptable salt thereof.

In yet another aspect, the invention features a synthetic peptide having the formula:

A-Tyr-Tyr-B-C-Tyr-Tyr-D-Tyr-Tyr-(Tyr-Tyr-B)$_n$ (SEQ ID NOS: 15–24)

wherein A is either any amino acid or is absent; B is either any amino acid or is absent; C is either any amino acid or is absent; D is either any amino acid or is absent; and n is 0 to 10, inclusive. In preferred embodiments, at least one of A, B, C, and D is not Tyr. In other preferred embodiments, A, B, C, or D are chosen from Ala, Cys, Asp, Glu, Phe, Gly, His, Ile, Lys, Leu, Met, Asn, Pro, Gln, Arg, Ser, Thr, Val, or Trp. In still other preferred embodiments, A is chosen from Ala, Cys, Asp, Glu, Phe, Gly, His, Ile, Lys, Leu, Met, Asn, Pro, Gln, Arg, Ser, Thr, Val, or Trp, and B, C, and D are chosen from Arg, Gln, Asp, Glu, Phe, or Trp. An exemplary peptide includes, without limitation, A-Tyr-Tyr-Arg-Arg-Tyr-Tyr-Arg-Tyr-Tyr (SEQ ID NO: 25); or a pharmaceutically acceptable salt thereof. In other embodiments, the peptide is linked to an immunological carrier.

In another aspect, the invention relates to short synthetic prion peptides (e.g., three to ten amino acids or four to twelve amino acids, inclusive) having antigencity as a PrP$^{Sc}$, including one or more of the following: a threonine tetrarepeat found at T189–193 of mouse PrP or the corresponding amino acid residues of human, sheep, goat, or bovine PrP; the M128, M133, or M153 amino acid residues of mouse PrP or the corresponding amino acid residues of human, sheep, goat, or bovine PrP; the H186 amino acid residue of mouse PrP or the corresponding amino acid residue of human, sheep, goat, or bovine PrP; the Q159, Q167, Q185, or Q216 amino acid residues of mouse PrP or the corresponding amino acid residues of human, sheep, goat, or bovine PrP; the N158 amino acid residue of mouse PrP or the corresponding amino acid residue of human, sheep, goat, or bovine PrP; the M128, M133, or M153 amino acid residues of mouse PrP or the corresponding amino acid residues of human, sheep, goat, or bovine PrP; the L124 or L129 amino acid residues of mouse PrP or the corresponding amino acid residues of human, sheep, goat, or bovine PrP; or the I181 or I183 amino acid residues of mouse PrP or the corresponding amino acid residues of human, sheep, goat, or bovine PrP.

Peptides according to the invention can be prepared by chemical synthesis according to methods known in the art.

In addition, a PrP peptide, according to the invention, can be used for preparing epitope-specific anti-PrP$^{Sc}$ antibodies. In particular, the peptide of the invention provides the advantages of a highly pure substance, and is suitable for preparing anti-PrP antibodies which can be used to detect PrP$^{Sc}$ in a sample, for example, in standard immunological assays such as immunoprecipitations, ELISA, and flow cytometry. The PrP peptide according to the invention (e.g., YYR) can be used to prepare both polyclonal epitope-specific anti-PrP$^{Sc}$ antibodies (antisera) and monoclonal epitope-specific anti-PrP antibodies. These antibodies are prepared according to standard methods known in the art, and are preferably bound to a carrier material for the generation of antibodies.

Moreover, compounds which exploit the PrP$^{Sc}$-specific exposure of YYX can be rationally designed or obtained from combinatorial libraries which mimic the interaction of YYX with anti-YYX antibodies. These compounds are useful in prion diagnostics or as therapies for prion diseases.

In another aspect, the invention features a pharmaceutical preparation for the therapy and prevention of prion diseases comprising a PrP peptide of the invention or structurally related compounds, or a polyclonal or monoclonal antibody in a pharmaceutical carrier. Such pharmaceuticals contain a PrP peptide or epitope-specific anti-PrP antibodies according to the invention.

If desired, the peptides and antibodies of the invention can be provided in the form of pharmaceutically acceptable salts. Examples of preferred salts are those with therapeutically acceptable organic acids, e.g., acetic, lactic, maleic, citric, malic, ascorbic, succinic, benzoic, salicylic, methanesulfonic, toluenesulfonic, or pamoic acid, as well as polymeric acids such as tannic acid or carboxymethyl cellulose, and salts with inorganic acids such as the hydrohalic acids, e.g., hydrochloric acid, sulfuric acid, or phosphoric acid. In addition, any of the peptides or antibodies of the invention may be administered to a mammal, particularly a human, in one of the traditional modes (e.g., orally, parenterally, transdermally, or transmucosally), in a sustained release formulation using a biodegradable biocompatible polymer, or by using micelles, gels, and liposomes.

In yet another aspect, the invention features a method of treating or preventing a prion disease in an animal (for example, a human, a bovine, sheep, pig, goat, dog, or cat). In one preferred embodiment, the method involves administering to the animal a therapeutically effective amount of epitope-specific anti-PrP antibody or PrP peptide that blocks the conversion of $PrP^C$ to $PrP^{Sc}$, inhibits $PrP^{Sc}:PrP^{Sc}$ aggregate formation, or blocks the recruitment of $PrP^C$ to $PrP^{Sc}$. The PrP peptide may also be used to immunize the host against prion disease by stimulating the production of host antibodies specific for $PrP^{Sc}$.

In related aspects, the invention features methods and kits for detecting $PrP^{Sc}$ in a biological sample.

In still another aspect, the invention features methods and kits for decontaminating $PrP^{Sc}$ from a biological sample. In a preferred embodiment, the method involves the steps of: (a) treating the biological sample with the polyclonal or monoclonal antibody (or a fragment or analog thereof), the treatment permitting antibody:$PrP^{Sc}$ complex formation; and (b) recovering the antibody:$PrP^{Sc}$ complex from the biological sample. Such a decontamination procedure may also involve the use of perfusing a biological sample with antibody (or a fragment or analog thereof) for the removal or inactivation of $PrP^{Sc}$.

In another aspect, the invention features a method for identifying a compound for the treatment of a prion disease. The method includes the steps of (a) measuring the binding of an anti-YYX antibody to $PrP^{Sc}$ in the presence of a test compound; and (b) measuring the binding of the anti-YYX antibody to $PrP^{Sc}$ in the absence of the test compound; wherein a level of binding of the anti-YYX antibody to $PrP^{Sc}$ in the presence of the test compound that is less than the level of binding of the anti-YYX antibody to $PrP^{Sc}$ in the absence of the test compound is an indication that the test compound is a potential therapeutic compound for the treatment of a prion disease. Preferably, the anti-YYX antibody is an anti-YYR antibody, anti-YYD antibody, or anti-YYQ antibody.

In another aspect, the invention features a method for identifying a compound for diagnosing a prion disease. The method includes the steps of: (a) measuring the binding of an anti-YYX antibody to $PrP^{Sc}$ in the presence of a test compound; and (b) measuring the binding of the anti-YYX antibody to $PrP^{Sc}$ in the absence of the test compound; wherein a level of binding of the anti-YYX antibody to $PrP^{Sc}$ in the presence of the test compound that is less than the level of binding of the anti-YYX antibody to $PrP^{Sc}$ in the absence of the test compound is an indication that the test compound is a potential compound useful for diagnosing a prion disease.

In related aspects, the invention features therapeutic and diagnostic compounds identified according to any of the aforementioned methods.

By "high binding affinity" is meant binding with an affinity constant of less than 10 μM, preferably, less than 1 μM, more preferably, less than 100 nM, and, most preferably, less than 10 nM.

By "prion diseases" is meant a group of prion-mediated, rapidly progressive, fatal, and untreatable brain degenerative disorders including, without limitation, Creutzfeldt-Jakob disease (CJD), variant CJD, iatrogenic CJD, familial CJD, Kuru, Gerstmann-Sträussler syndrome, and fatal familial insomnia in humans (Prusiner, *Science* 252:1515–1522, 1991), scrapie in sheep and goats, and spongiform encephalopathy in cattle, as well as recently described prion diseases in other ruminants and cats.

By "treatment of prion diseases" is meant the ability to reduce, prevent, stabilize, or retard the onset of any symptom associated with prion diseases, particularly those resulting in spongiform change, neuronal cell loss, astrocytic proliferation, accumulation of $PrP^{Sc}$ protein, dementia, or death.

By "purified antibody" is meant antibody that is at least 60%, by weight, free from the proteins and naturally-occurring organic molecules with which it is naturally associated. Preferably, the preparation is at least 75%, more preferably at least 90%, and most preferably at least 99%, by weight, antibody, e.g., YYX-specific antibody (e.g., a YYR-, YYQ-, or YYD-specific antibody). A purified antibody may be obtained, for example, by affinity chromatography using substrate-bound YYX and standard techniques.

By "YYX" is meant a peptide having the sequence Tyrosine-Tyrosine-X, where X is any amino acid. By "YYR" is meant a peptide having the sequence Tyrosine-Tyrosine-Arginine. By "YYQ" is meant a peptide having the sequence "Tyrosine-Tyrosine-Glutamine." By "YYD" is meant a peptide having the sequence "Tyrosine-Tyrosine-Aspartic acid."

By a "therapeutic composition" is meant a composition appropriate for administration to an animal, for example, a mammal, such as a human, a livestock species (for example, a bovine, goat, pig, or sheep), or a pet species.

By a "small molecule" is meant a compound with a molecular weight of less than or equal to 10,000 Daltons, preferably, less than or equal to 1000 Daltons, and, most preferably, less than or equal to 500 Daltons.

Other features and advantages of the invention will be apparent from the following description of the preferred embodiments thereof, and from the claims.

BRIEF DESCRIPTION OF THE DRAWINGS

FIG. 1A is a graph showing circular dichroism of pH-related conformational changes in mouse recombinant $PrP^{C}$. Far-UV circular dichroism spectroscopy of $PrP^{C}$ at pH of 7.0 and 3.0 shows a shift in molecular ellipticity consistent with a change in conformation from predominantly alpha helix at physiological pH to predominantly beta sheet at low pH.

FIG. 1B is a plot showing the fluorescence spectroscopy of pH-related changes in aromatic ring orientation in mouse recombinant $PrP^{C}$. Changes in specific fluorescence of tyrosine and tryptophan side chains are consistent with opposing tendencies for solvent accessibility as pH is reduced.

FIG. 2 shows the alignment of PrP amino acid sequences from bovine (SEQ ID NO: 26), man (SEQ ID NO: 27), sheep (SEQ ID NO: 28), mouse (SEQ ID NO: 29), and hamster (SEQ ID NO: 30). The boxes highlight the two highly conserved YYR sequences at amino acids 160–162 and 173–175, as well as the YYQ/D sequence at amino acids 235–237 (according to the bovine sequence).

FIG. 3 shows an NMR solution structure of mouse $PrP^{C}$, highlighting the location and orientation of the YYR and YYD sequences. None of the YY motifs show the so-called orthogonal tandem orientation of aromatic rings to the molecular surface.

Figure 3:
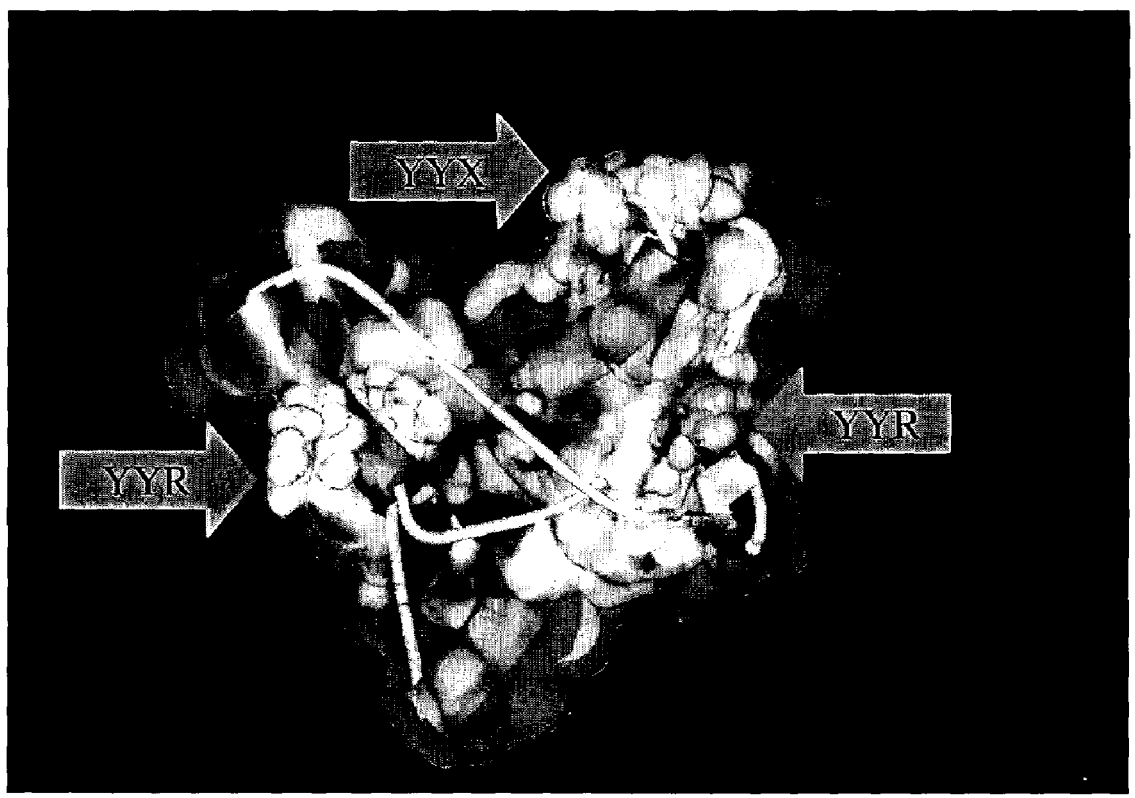
Figure 4:
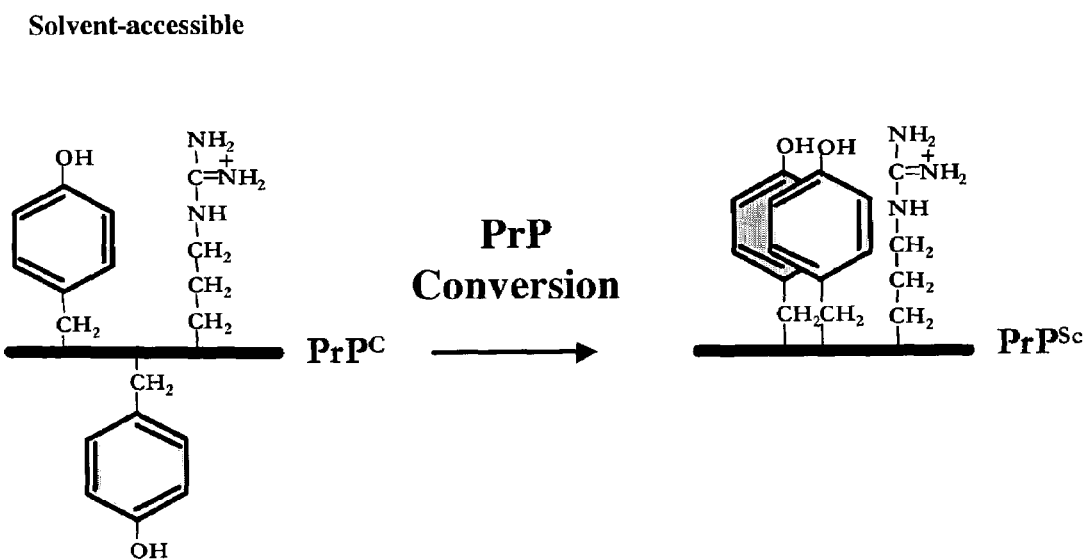

FIG. 4 is a schematic showing epitope generation based on a change in tyrosine ring orientation that occurs with conformational change of PrP$^C$ to PrP$^{Sc}$. As depicted in FIG. 3, two YYR motifs in PrP$^C$ are oriented such that one tyrosine ring is solvent-accessible, whereas the other is solvent-inaccessible in the molecular interior. (The third YY motif, not shown in this schematic, is oriented such that the tyrosine rings are unable to interact). Upon PrP conformational conversion, tyrosine rings in one or more YYX motif become accessible at the molecular surface in an orthogonal tandem orientation that is stabilized by pi-stacking interactions. The terminal planar arginine (or aspartate/glutamine in the third motif) may additionally stabilize the tyrosine-tyrosine interaction.

Figure 5:
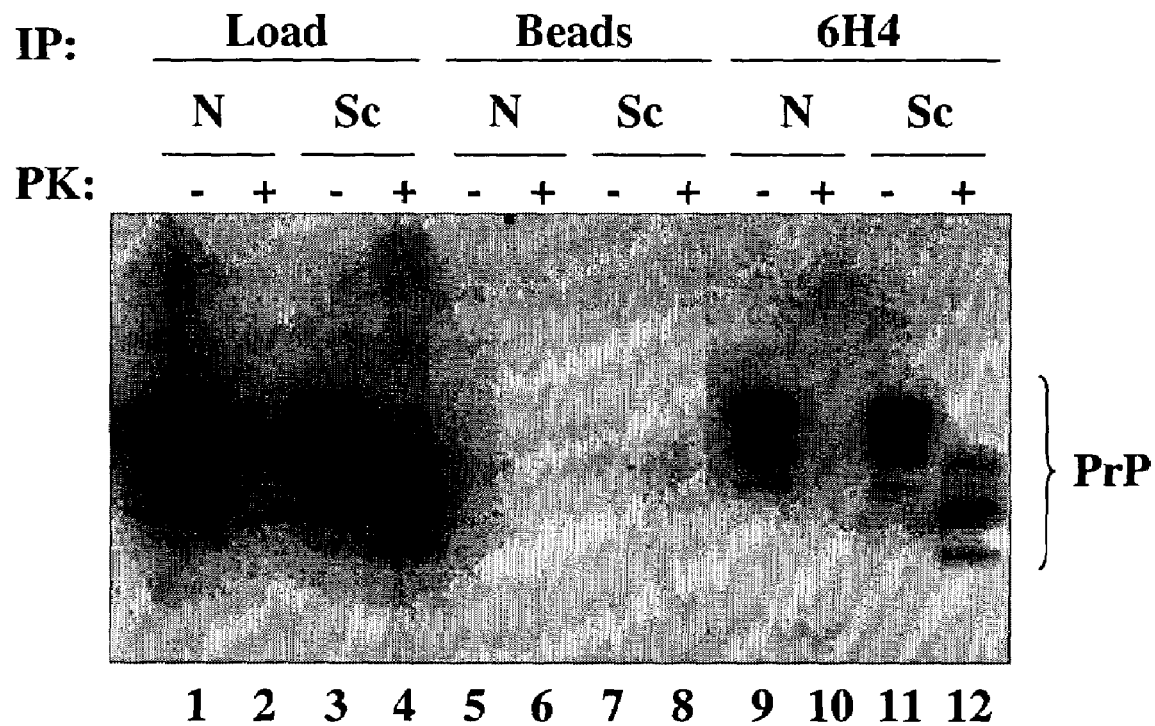

FIG. 5 shows the immunoprecipitation (IP) of mouse PrP$^{Sc}$ using magnetic beads conjugated to control proteins. Non-distinguishing PrP monoclonal antibody 6H4 coupled to magnetic beads (lanes 9–12) or beads coupled to BSA (beads, lanes 5–8) were reacted with normal (N) or ME7 scrapie infected (Sc) mouse brain homogenates. The brain homogenates were treated with proteinase K (+) or not (−) prior to the immunoprecipitation. In lanes 1–4 (Load) are displayed direct western blots of the same amount of brain homogenates that were used in the immunoprecipitations. The immunoprecipitates were resolved on SDS-PAGE gels under non-reducing conditions. Blots were probed with 6H4 monoclonal antibody followed by goat anti-mouse Ig-HRP conjugate.

Figure 6:
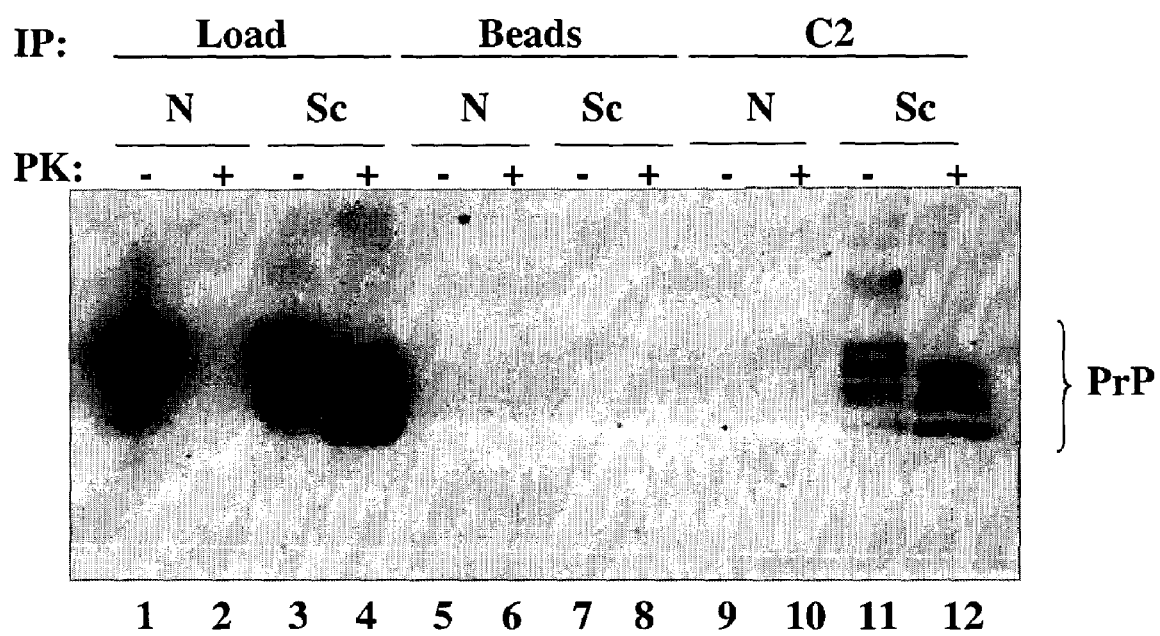

FIG. 6 shows the immunoprecipitation (IP) of mouse PrP$^{Sc}$ using magnetic beads conjugated with the anti-YYR polyclonal antibody pAbC2. pAbC2-coupled magnetic beads (lanes 9–12) or beads coupled to BSA (beads, lanes 5–8) were reacted with normal (N) or ME7 scrapie infected (Sc) mouse brain homogenates. The brain homogenates were treated with proteinase K (+) or not (−) prior to the immunoprecipitation. In lanes 1–4 (Load) are displayed direct western blots of the same amount of brain homogenates that were used in the immunoprecipitations. The immunoprecipitates were resolved on SDS-PAGE gels under non-reducing conditions. Blots were probed with 6H4 monoclonal antibody followed by goat anti-mouse Ig-HRP conjugate.

Figure 7:
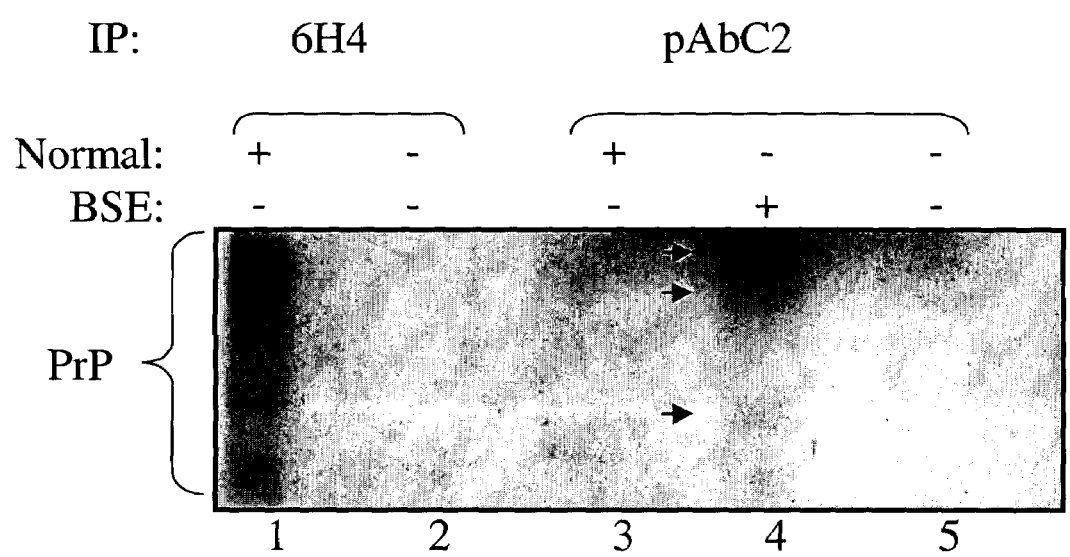

FIG. 7 shows the immunoprecipitation of bovine PrP$^{Sc}$ using magnetic beads conjugated with pAbC2 rabbit polyclonal antibody. 6H4 (lanes 1 and 2) or pAbC2-coupled magnetic beads (lanes 3 and 4) were used to immunoprecipitate normal or BSE brain homogenates. The immunoprecipitates were resolved on SDS-PAGE gels under non-reducing conditions. Blots were probed with 6H4 monoclonal antibody followed by goat anti-mouse Ig-HRP conjugate.

Figure 8:
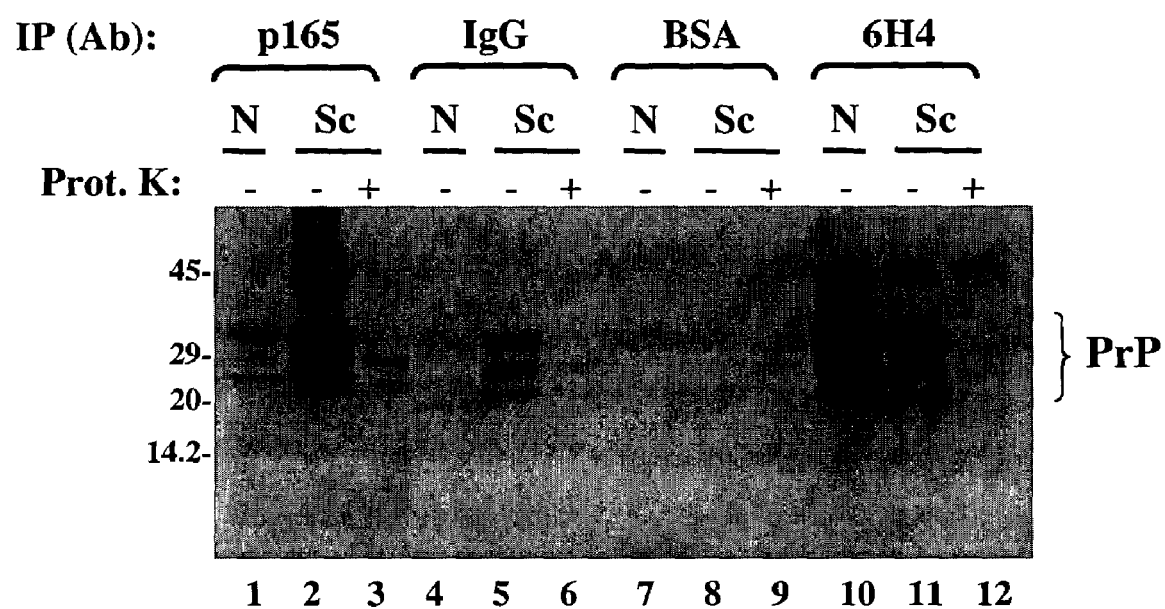

FIG. 8 shows the immunoprecipitation of mouse PrP$^{Sc}$ using magnetic beads conjugated with the anti-YYR p165 goat polyclonal antibody. Antibody-coupled magnetic beads were reacted with normal (N) or ME7 scrapie infected (Sc) mouse brain homogenates. The scrapie samples were treated with proteinase K (+) or not (−) prior to the immunoprecipitation. Lanes 1–3 (p165) affinity-purified goat pAb; Lanes 4–6 (IgG) total goat IgG; Lanes 7–9 (BSA) BSA-conjugated beads; Lanes 10–12 (6H4) non-discriminating anti-PrP monoclonal antibody 6H4. The immunoprecipitates were resolved on SDS-PAGE gels under non-reducing conditions. Blots were probed with 6H4 monoclonal antibody followed by goat anti-mouse Ig-HRP conjugate.

Figure 9:
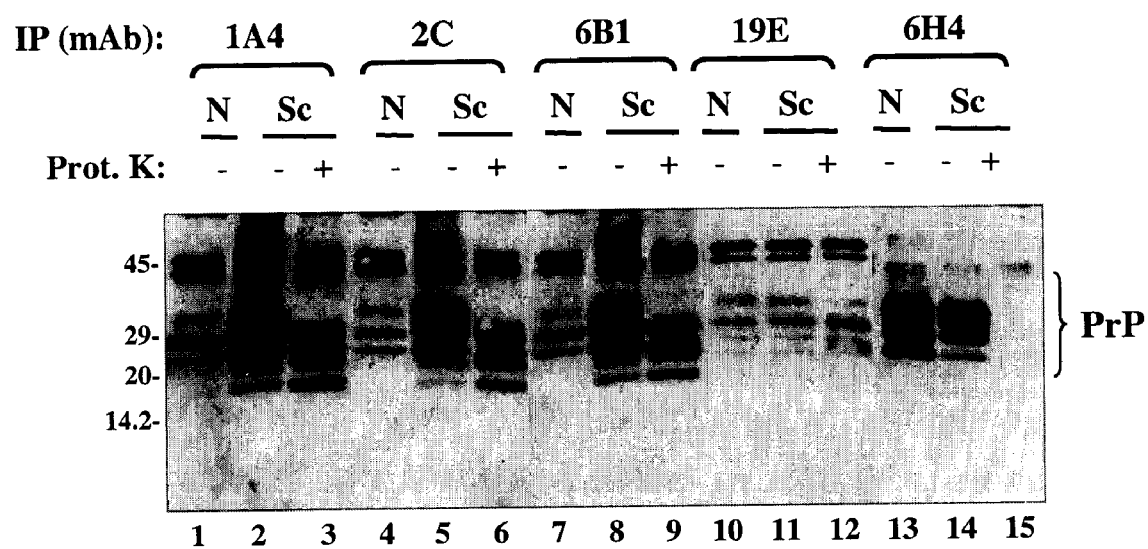

FIG. 9 shows the immunoprecipitation of mouse PrP$^{Sc}$ using magnetic beads conjugated to anti-YYR mouse monoclonal antibodies. Monoclonal antibody-coupled magnetic beads were reacted with normal (N) or ME7 scrapie infected (Sc) mouse brain homogenates. The scrapie samples were treated with proteinase K (+) or not (−) prior to the immunoprecipitation. 1A4 (lanes 1–3), 2C (lanes 4–6), and 6B1 (lanes 7–9) are scrapie reactive monoclonal antibodies. 19E (lanes 10–12) is a monoclonal antibody unreactive with PrP. 6H4 (lanes 13–15) is an anti-PrP monoclonal antibody that does not discriminate PrP$^C$ from PrP$^{Sc}$. The immunoprecipitates were resolved on SDS-PAGE gels under non-reducing conditions. Blots were probed with 6H4 monoclonal antibody followed by goat anti-mouse Ig-HRP conjugate. In lanes 10–12, corresponding to 19E, immunoglobulin heavy (45 kDa) and light (30 kDa) chain from the antibody-bead conjugates co-migrate with PrP dimers, and one of the PrP glycosylation variants, respectively.

Figure 10:
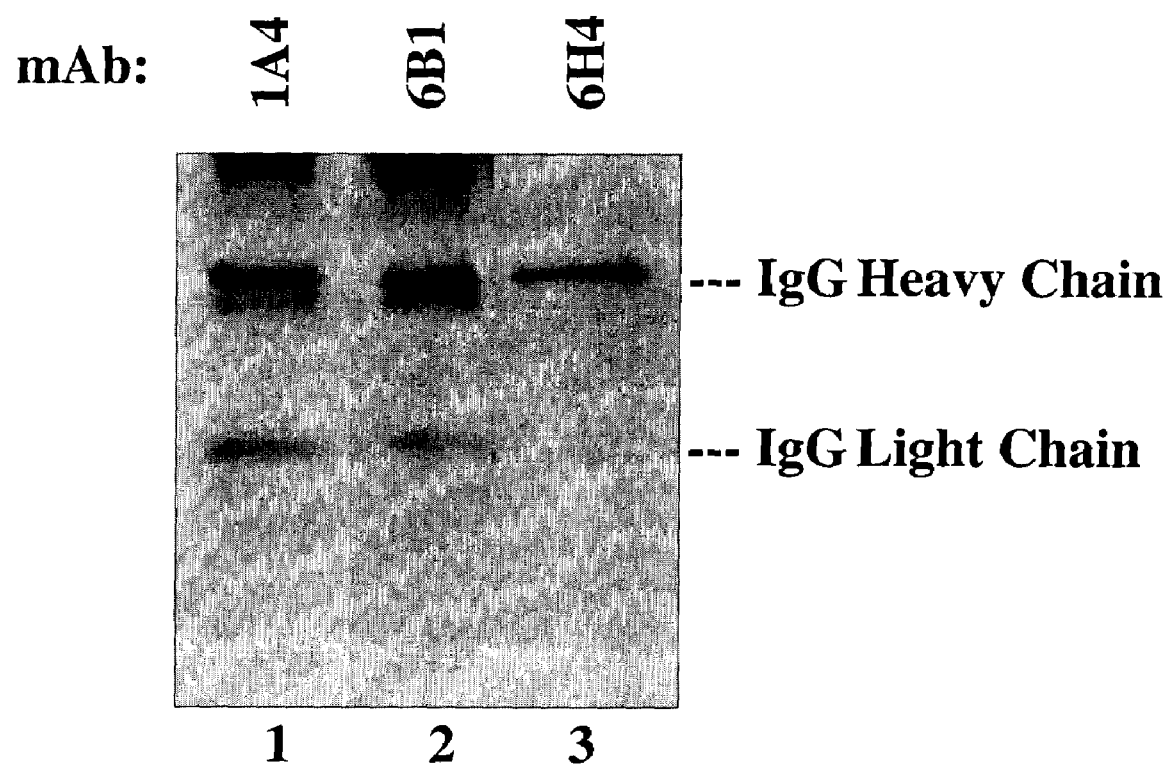

FIG. 10 shows the immunoglobulin light chain and heavy chain leakage from the antibody-bead conjugates. Monoclonal antibody 1A4 and 6B1 magnetic beads conjugates were processed for SDS PAGE and western blot analysis in the absence of brain homogenates. SDS-PAGE gels were run under non-reducing conditions for these two antibody-bead conjugates and under reducing conditions for the unconjugated 6H4 monoclonal antibody. Blots were developed with goat anti-mouse Ig-HRP conjugates.

Figure 11:
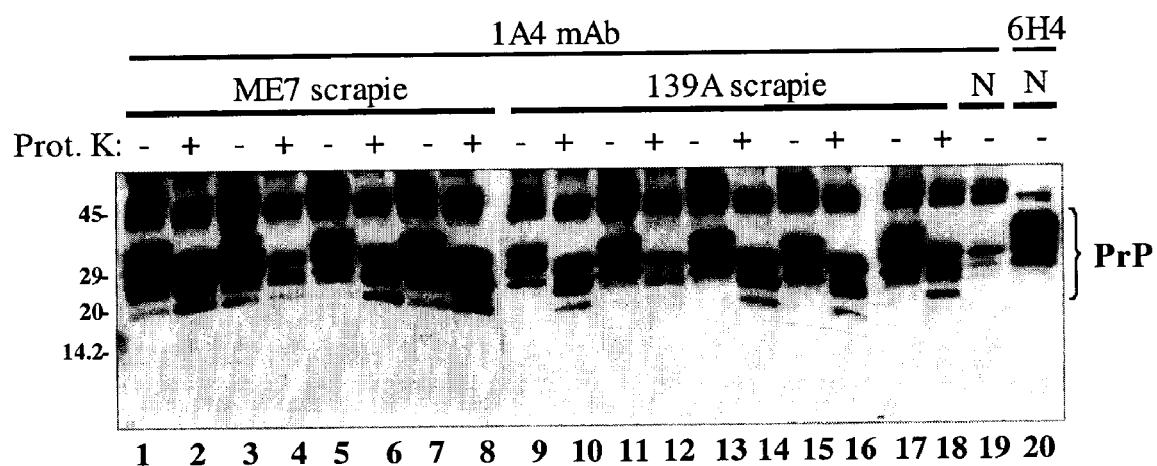

FIG. 11 shows the immunoprecipitation of multiple mouse PrP$^{Sc}$ samples using magnetic beads coupled with the anti-YYR 1A4 monoclonal antibody. 1A4-magnetic bead conjugates were reacted with normal (N, lane 19), four ME7 (lanes 1–8), or five 139A (lanes 9–18) scrapie infected mouse brain homogenates. The scrapie samples were treated with proteinase K (+) or not (−) prior to the immunoprecipitation. 6H4-magnetic bead conjugates were reacted with normal (N, lane 20) mouse brain homogenates as a control. The immunoprecipitates were resolved on SDS-PAGE gels under non-reducing conditions. Blots were probed with 6H4 monoclonal antibody followed by goat anti-mouse Ig-HRP conjugate.

Figure 12:
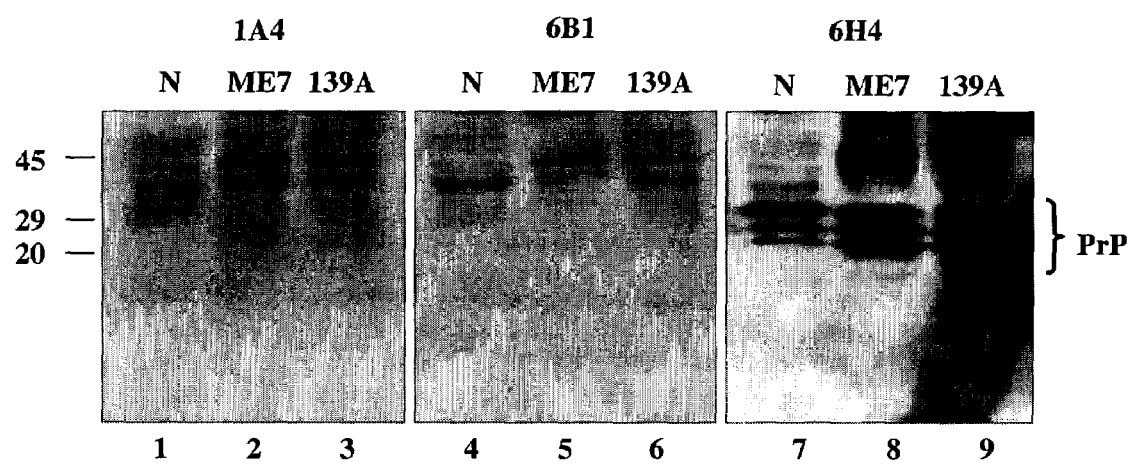

FIG. 12 shows the conformation dependence of anti-YYR monoclonal antibody reactivity to PrP$^{Sc}$. Normal (N), ME7, and 139A scrapie infected mouse brain homogenates were resolved in SDS-PAGE gels under non-reducing conditions. Blots were probed with 1A4 (lanes 1–3) or 6B1 (lanes 4–6) followed by goat anti-mouse Ig-HRP conjugates. The blots were then re-probed, without stripping, using 6H4 (lanes 7–9) and goat anti-mouse Ig-HRP conjugates.

Figure 13:
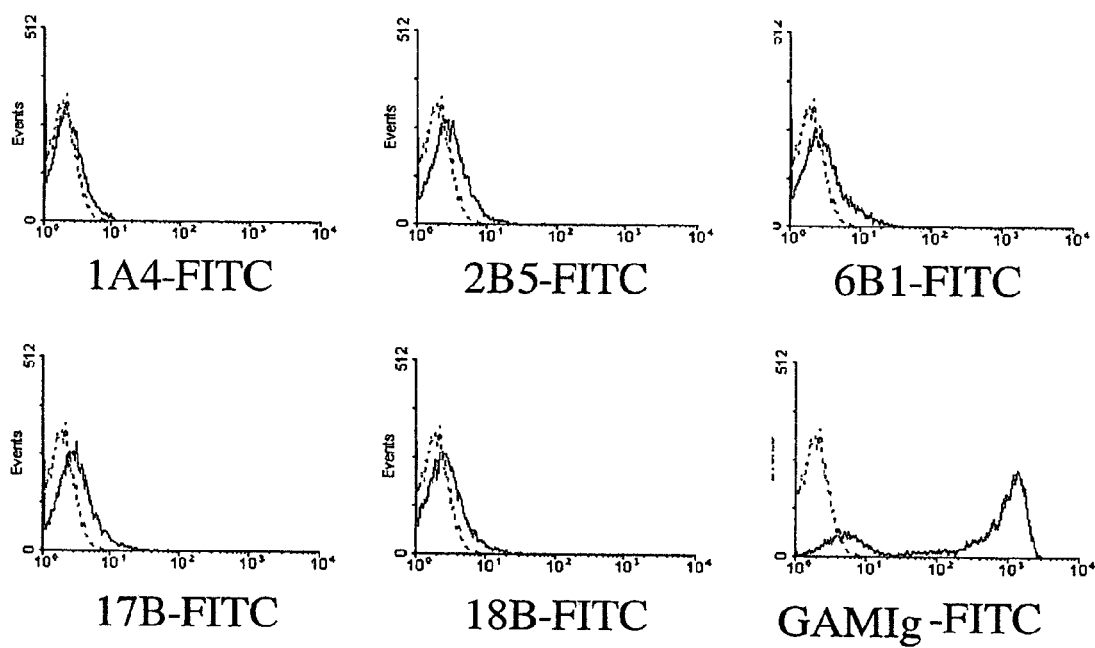

FIG. 13 shows an analysis of dissociated normal mouse splenocytes reacted with fluoresceinated anti-PrP$^{Sc}$ monoclonal antibodies 1A4, 2B5, 6B1, 17B, and 18B using flow cytometry. Fluoresceinated goat anti-mouse Ig (GAMIg) was used as a control. Cells were gated on acquisition by characteristic forward and side scatter parameters and for exclusion of propidium iodide. The dashed lines represent background fluorescence; solid lines represent antibody staining. The monoclonal antibodies were successfully fluorescein labelled as measured by fluorescein emission in a 96-well plate reader and maintained their reactivity towards the immunizing antigen by ELISA.

Figure 14:
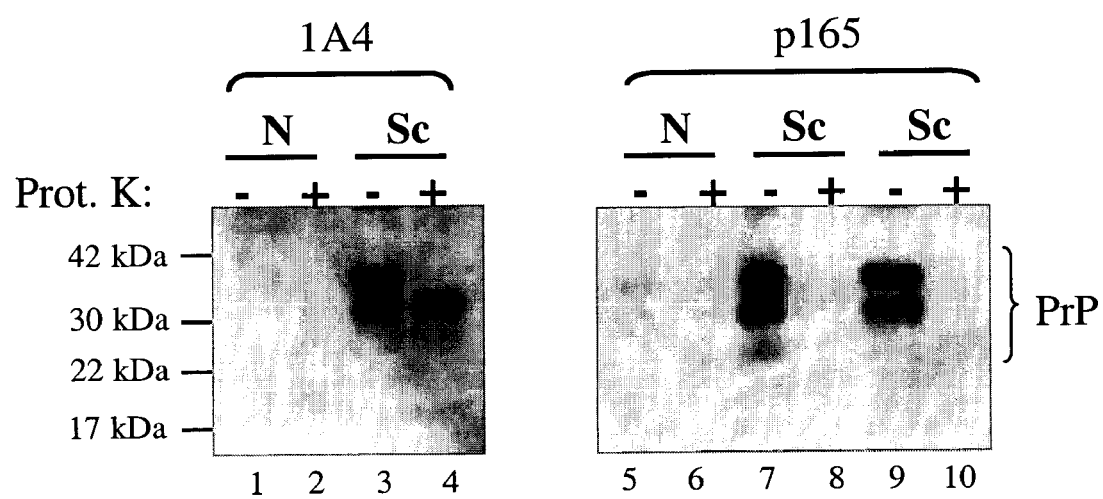

FIG. 14 shows the immunoprecipitation of hamster PrP$^{Sc}$ using anti-YYR mouse monoclonal antibody and goat polyclonal antibody. 1A4 monoclonal antibody and p165 polyclonal antibody-magnetic bead conjugates were reacted with normal (N) or scrapie infected hamster brain homogenates (Sc). The scrapie samples were treated with proteinase K (+) or not (−) prior to the immunoprecipitation. The immunoprecipitates were resolved on SDS-PAGE gels under non-reducing conditions. Blots were probed with 6H4 monoclonal antibody followed by goat anti-mouse Ig-HRP conjugate.

Figure 15:
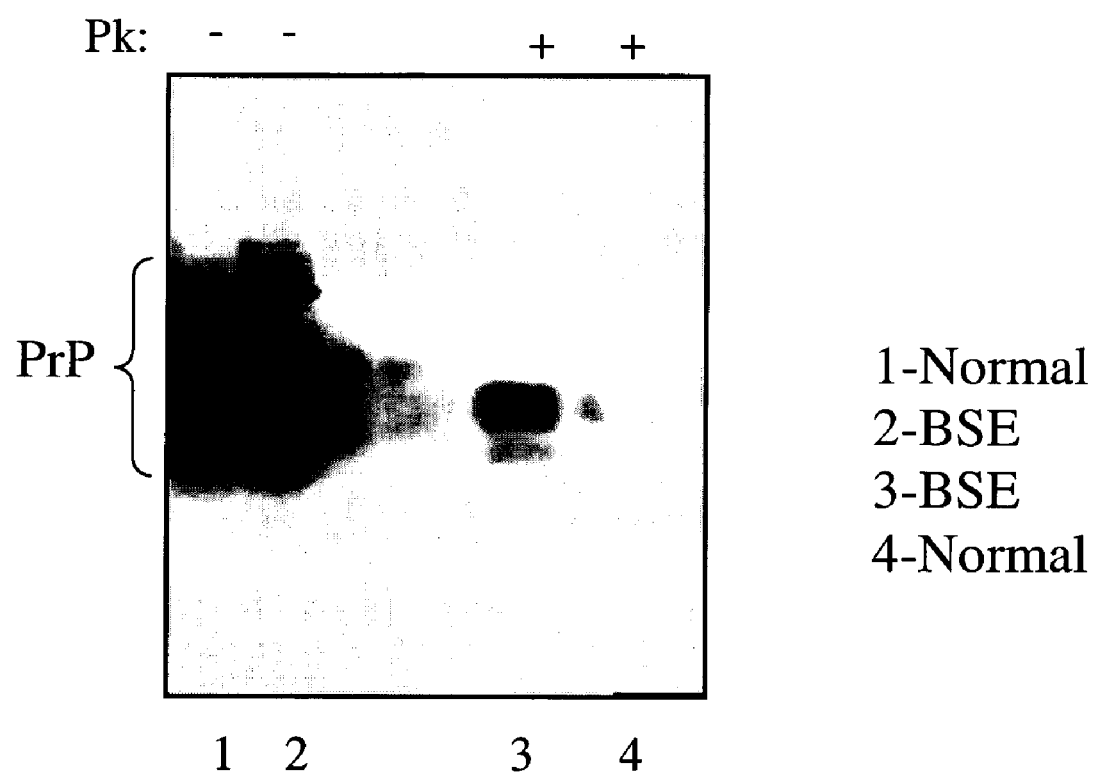

FIG. 15 shows an immunoblot detection of protease-sensitive PrP$^C$ in normal bovine brain (lanes 1 and 4), and PrP$^C$ and protease-resistant PrP$^{Sc}$ in BSE brain (lanes 2 and 3). Brain homogenates treated or not treated with proteinase K (+ or −) were resolved on SDS-PAGE electrophoresis, and transferred onto a PVDF membrane for immunblotting. The membrane was probed with mAb 6H4, washed, and developed with ECL and exposed to X-ray film according to standard procedures.

FIG. 16 shows ELISA systems demonstrating specific bovine PrP$^{Sc}$ recognition by the anti-YYR rabbit polyclonal antibody pAbC2. BSE brain extract reacted with ELISA-adsorbed soluble prion receptor ectodomain (PC2) or control protein (Mek) showed statistically significant detection by pAbC2 of bound PrP$^{Sc}$ in receptor vs control wells (Panel A; p-value=0.008). The recognition of recombinant bovine PrP$^C$ (bPrP) by direct ELISA with pAbC2 or mAb6H4 is also shown (Panel B).

DETAILED DESCRIPTION OF THE INVENTION

We have determined that the orientation of selected aromatic side chains of tyrosines of a YYX epitope (e.g., YYR) at one or more sites in PrP defines a continuous immunologic epitope specific for the molecular surface of PrP$^{Sc}$, whereas the same tyrosine side chains are known to be inaccessible in the PrP$^C$ conformation, according to published PrP$^C$ NMR structure solutions (Riek et al., *Nature* 382:180, 1996; Donne et al., *Proc. Natl. Acad. Sci. USA*, 94:13452–7, 1997; Zahn et al, *Proc. Natl. Acad. Sci. USA*, 97:145–50, 2000). This discovery facilitates the generation of PrP$^{Sc}$-specific antibodies which may be used for diagnostic and therapeutic purposes, as well as the development of screens for novel compounds useful to detect or combat prions and their related diseases and disorders.

Generation of Epitope-Specific Antibodies to PrP$^{Sc}$

Antibodies specifically recognize proteins via unique amino acid determinants or epitopes. These determinants or epitopes may be of a linear amino acid sequence or distinct conformations formed by amino acids in three-dimensional space. Considering conversion of PrP$^C$ to PrP$^{Sc}$ involves a major change in protein conformation, it is likely that unique epitopes will be formed or revealed upon conversion. Therefore, as is discussed herein, we have developed a so-called side chain hypothesis pertaining to prion protein conversion. According to this scheme, side chains normally sequestered in the solvent-inaccessible interior of PrP$^C$ may be solvent accessible in PrP$^{Sc}$. The preponderance of newly exposed side chains are therefore expected to be hydrophobic, as evidenced by increased solvent exposure of hydrophobic residues in a stable PrP$^{Sc}$-like intermediate (Swietnicki et al, *J. Biol. Chem.* 272:27517–20, 1997). The extrusion of these hydrophobic side chains, alone or in combination with side chains that are normally present on the molecular surface of PrP$^C$, form the basis of unique epitopes for antibody recognition of PrP$^{Sc}$. Moreover, these surface-accessible hydrophobic side chains are expected to change the solubility and aggregation characteristics of PrP$^{Sc}$, commensurate with the known properties of this structural isoform. Newly accessible side chains may also participate in the process of recruitment of PrP$^C$ to PrP$^{Sc}$.

Testing this hypothesis began in vitro by examining the orientation of tryptophan and tyrosine rings, two hydrophobic amino acid side chains for which information was obtained by fluorescence spectroscopic studies. First, a beta sheet transition of mouse recombinant PrP$^C$ was induced by low pH in order to model the structural changes that characterize the conversion of PrP$^C$ to PrP$^{Sc}$ (Hornemann and Glockshuber, *Proc. Natl. Acad. Sci.* 95:6010, 1998). FIG. 1A demonstrates a shift in molecular ellipticity by circular dichroism from a pH of 7.0 to 3.0 consistent with a change of PrP$^C$ from predominantly alpha helix to predominantly beta sheet (spectra shifting from double to single minima at appropriate respective frequencies).

Figure 1B:
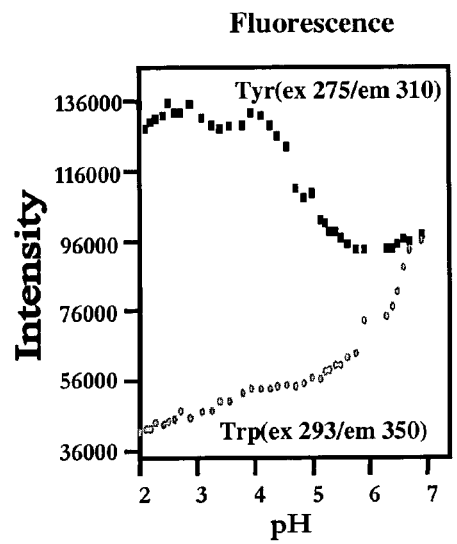

Second, the solvent accessibility of tyrosine and tryptophan side chains in recombinant PrP$^C$ with pH titration was examined using standard fluorescence spectroscopy (FIG. 1B). This study is based on the principle that aromatic side chains which are neighboring other amino acid side chains (i.e., in the interior of the protein) will possess a different specific fluorescence than aromatic side chains exposed to water (for example, Chin et al, *Biochemistry* 31:1945–51,1992). When recombinant mouse PrP$^C$ was subjected to low pH, tryptophan and tyrosine aromatic groups displayed opposing behaviors consistent with differential solvent exposure.

Inspection of the amino acid sequence of human, bovine, and murine PrP$^C$ revealed thirteen tyrosine residues (FIG. 2). Eleven tyrosines in human and bovine PrP and 10 in murine PrP are contained in the C-terminal ⅔ of the protein, which comprises the protease-resistant structured domain necessary and sufficient for prion infectivity. Remarkably, six tyrosines in this domain are present in the unusual "YY" paired motif (FIG. 2). Two of the three pairs are in conjunction with a C-terminal arginine (R), whereas the third YY motif is in conjunction with a C-terminal aspartate (D) in mice and hamsters or a glutamine (Q) in cattle, sheep, and humans. R contains a terminal guanido group, whereas Q and D contain carboxamide and carbonyl bonds, which are planar. Such a terminal planar amino acid in the YY motif may interact with the exposed tyrosine rings to stabilize or shepherd them for immune recognition.

In addition, inspection of the NMR-resolved structures of murine, hamster, and human PrP$^C$ revealed that none of the identified tyrosine pairs are oriented with both of their rings in an orthogonally tandem configuration accessible on the molecular surface (Riek et al., *Nature*, 382:180, 1996; Donne et al., *Proc. Natl. Acad. Sci.*, 94:13452, 1997; Zahn et al, *Proc. Natl. Acad. Sci. USA*, 97:145–50, 2000) (FIG. 3). It is reasonable to surmise that the increased exposure of tyrosine on the surface of acid-treated PrP$^C$ or PrP$^{Sc}$ is associated with some of the tyrosine pairs. One stable conformation of tyrosine rings is referred to as pi-stacking, in which the two rings are stacked in slightly displaced parallel manner (schematically illustrated in FIG. 4). Although stable, a preliminary search of the structural databases for pi-stacked surface accessible tyrosine rings identified only 4 other proteins with similar orientation, none of which are in the ectodomain of membrane proteins. Therefore, a novel PrP$^{Sc}$-specific epitope is thought to be tyrosine pairs in a pi-stacking orientation, with or without the contribution of side chains of arginine, glutamine, and aspartate (which, being planar, may also participate in a pi-stacking interaction with its preceding tyrosine).

In addition to changes in orientation of tyrosine side chains in PrP$^{Sc}$, it is also possible that the three YYR motifs become more immunologically accessible in PrP$^{Sc}$ because of shifts in their proximity to each other. A typical IgG antibody is comprised of two identical antigen-binding regions that are connected to one constant region by a flexible hinge region. During the conformational change of PrP$^C$ to PrP$^{Sc}$, YYR motifs probably move relative to each other (Korth et al., *Nature,* 390:74–77, 1997), moving from relatively separated to relatively close. In addition, IgG recognition of YYR motifs in PrP$^C$ may be unfavorable because two critical motifs are on different sides of the molecule, rendering the recognition to be of a low-avidity univalent nature, rather than the high-avidity interaction in which both IgG antigen binding regions participate in recognition.

Our data with bovine PrP$^C$ and PrP$^{Sc}$ showed that anti-YYR antibodies specifically recognize PrP$^{Sc}$ by immunoprecipitation and ELISA testing (see below), consistent with changes in the accessibility of tyrosine side chains in PrP$^{Sc}$ and/or proximity of the YYR epitopes. The amino acid residue, arginine, is also thought to be important in the generation and recognition specificity of the YYR antibody. It is believed that electrostatic interaction between polar tyrosine side chains and the highly basic side chain of arginine contribute to the nature of the YYR epitope in both immunization by the YYR tripeptide, and the recognition of PrP$^{Sc}$ by the derived antibody. It is notable that the third YY dimer motif in the terminal PrP loop is associated with a glutamine in some species (including humans and cattle), which is a partially conservative substitution with arginine, and aspartate in some other species (including mice and hamsters), which is not a conservative substitution. Exemplary amino acids having planar side chains include arginine, aspartate, and glutamine.

The phenomenon of amino acid side chain exposure incident on conformational conversion of PrP$^C$ to PrP$^{Sc}$ may not uniquely apply to tyrosine pairs. It is possible that other amino acids with bulky side chains may find these side chains to be poorly tolerated in the core of PrP$^{Sc}$, and that these side chains, alone or in combination with other local moieties, form the basis of unique immunoreactivity of PrP$^{Sc}$. Immunological epitopes differing between PrP$^C$ and PrP$^{Sc}$ form the basis of a diagnostic test for PrP$^{Sc}$, and are also useful in the treatment and immunization of humans and animals against prion disease. Hydrophobic side chain exposure is thought to be responsible for the increased hydrophobicity and enhanced aggregation of PrP$^{Sc}$ compared to PrP$^C$.

Examples of bulky side chains not fully accessible to solvent in PrP$^C$ include the following (amino acid residues are numbered according to the mouse PrP sequence):

1. Tyrosines not contained in the YYX motif, including Y127, Y156, Y217.
2. A threonine tetrarepeat, T189–193, partially not exposed to solvent.
3. Histidine H186.
4. Glutamine Q159, Q167, Q185, Q216.
5. Asparagine N158.
6. Methionine M128, M133, M153.
7. Leucine L124, L129.
8. Isoleucine I181, I183.

As is described below, peptides containing the YYR epitope were synthesized. These peptides were conjugated to a carrier and used to immunize rabbits or mice for the production of polyclonal or monoclonal antibodies. Polyclonal and monoclonal antibodies were then tested for specificity to PrP$^{Sc}$. The results indicated that such antibodies bound specifically, with high binding affinity to PrP$^{Sc}$.

The following examples described below are provided for the purpose of illustrating the invention, and should not be construed as limiting.

PrP$^{Sc}$-Specific Antibodies

Polyclonal antisera, pAbC2, were raised in rabbits against a YYR peptide linked to KLH. Serum was collected from each rabbit after the immunization regime and total IgG purified using a Protein A column. Anti-PrP$^{Sc}$ activity of these samples was then tested in immunoprecipitation reactions using brain homogenates from normal or scrapie-infected mice. Initial analysis of the brain homogenates used in these studies revealed detectable amounts of PrP$^C$ in normal brain extracts (FIG. 5, lane 1) and PrP in infected samples (FIG. 5, lane 3). As expected, PrP$^C$ was sensitive to digestion by proteinase K (PK) (FIG. 5, lane 2), whereas the characteristic migration shift of the protease-resistant core of PrP$^{Sc}$ (designated PrP 27–30) was evident upon PK digestion (FIG. 5, lane 4). Incubation of these brain homogenates with BSA-coupled magnetic beads failed to precipitate any detectable PrP (FIG. 5, lanes 5–8), whereas, incubation of the samples with beads coupled with 6H4 (a PrP-specific monoclonal antibody) immunoprecipitated PrP$^C$ from normal brains (FIG. 5, lane 9), and PrP$^{Sc}$ (FIG. 5, lane 11) and PrP 27–30 (FIG. 5, lane 12) from infected brains. When pAbC2 IgG was coupled to the beads and incubated with normal brain homogenates, no detectable PrP was immunoprecipitated (FIG. 6, lanes 9 and 10). Strikingly, incubation of the pAbC2 IgG-coupled beads with infected samples immunoprecipitated PrP$^{Sc}$ (FIG. 6, lane 11) and PrP 27–30 (FIG. 6, lane 12). Once again, these tissues harbored detectable amounts of PrP$^C$ and PrP$^{Sc}$ (FIG. 6, lanes 1–4) and BSA-coupled beads failed to immunoprecipitate any PrP (FIG. 6, lanes 5–8).

In addition, similar experiments showed that pAbC2 IgG specifically immunoprecipitates bovine PrP$^{Sc}$ from BSE infected brains compared to 6H4 (FIG. 7). Moreover, pAbC2 antibodies can recognize bovine PrP$^{Sc}$ in an ELISA system using soluble PC2 (prion receptor) as a capture reagent, but generates no signal in ELISA studies in which recombinant bovine PrP$^C$ is directly adsorbed to plates, despite its detectability using the 6H4 monoclonal antibody (FIG. 16). Anti-YYR IgG does not recognize denatured recombinant bovine PrP$^C$ in western blotting (data not shown), similar to studies detailed below with mouse anti-YYR monoclonal antibodies.

A goat polyclonal antisera was also raised to YYR linked to KLH. Serum was collected and total IgG was isolated by ammonium sulfate precipitation. YYR-reactive IgG was also purified from the same sera by affinity chromatography using a YYR-conjugated column. These antisera were subjected to a similar set of screening and validating immunoprecipitation reactions as detailed above. One of the three immunized goats developed antiserum (p165) that was specific for PrP$^{Sc}$ (FIG. 8) and was further characterized. As in previous experiments, 6H4-coupled beads non-discriminately precipitated both PrP$^C$ and PrP$^{Sc}$ from infected mouse brains (FIG. 8, lanes 10 and 11). No 6H4 immunoprecipitation of PrP 27–30 was seen in this experiment (FIG. 8, lane 12), as is occasionally observed for unknown reasons. When total IgG from immunized goats was coupled to the beads, little, if any, material was precipitated from normal and infected mouse brain homogenates (FIG. 8, lanes 4, 5 and 6). In contrast, when YYR-affinity purified IgG (p165) was coupled to the magnetic beads, only PrP$^{Sc}$ was precipitated from infected mouse brains (FIG. 8, lane 2). Unlike the pAbC2 polyclonal from rabbits, the goat anti-YYR polyclonal did not precipitate PrP 27–30 (FIG. 8, lane 3). These extracts contained detectable PrP 27–30 following PK digest, as simultaneous experiments evaluating monoclonal antibodies (see below) used the same homogenates and PrP 27–30 was detected upon PK digestion (FIG. 9, lanes 3, 6 and 9). Moreover, analysis of the brain homogenates by western blot revealed detectable PrP$^{Sc}$ and PrP 27–30 in the brain homogenates from infected mice (data not shown).

In addition to the goat polyclonal antibody generation, monoclonal antibodies against the same PrP$^{Sc}$-specific epitope were also generated, but with a derivative of the original antigen in which multiples of the original YYR peptide were linked together into one contiguous sequence. YYRRYYRYY (SEQ ID NO: 31) was synthesized in an attempt to increase the number of YYR epitopes in the peptide sequence, and to increase the chance of tyrosine stacking and/or frequency of pi-stacking. Moreover, one of the YYR sequences in the prion protein is preceded by an arginine in the five species of interest (FIG. 2). The YYR-RYYRYY peptide was linked to KLH and mice were subsequently immunized with the antigen. Splenocytes from these mice were isolated and fused to the FO murine B cell line (ATCC CRL-1646) to generate specific hybridoma clones. Ascities were produced from clones that reacted with YYR conjugated to an alternative carrier, 8map, in an ELISA. IgG from these ascities were purified using a Protein-A column and screened and validated using standard methods. Five monoclonal antibodies were identified that specifically recognized PrP$^{Sc}$ in immunoprecipitation reactions using brain homogenates from infected mice (1A4, 6B1, 2B5, 2C, and 18B). FIG. 9 illustrates the specific precipitation of PrP$^{Sc}$ for three of these monoclonal antibodies, 1A4, 2C, and 6B1. As was seen for p165, 1A4, 2C, and 6B1 specifically precipitated PrP$^{Sc}$ (FIG. 9, compare lanes 1, 3 and 5 with lanes 2, 4 and 6 respectively) compared to a negative control antibody, 19E (FIG. 9, lanes 10 and 11), and the non-distinguishing antibody 6H4 (FIG. 9, lanes 14 and 15). In contrast to p165, all three of these PrP$^{Sc}$-specific antibodies precipitated PrP 27–30 (FIG. 9, lanes 3, 6 and 9). The faint bands present in the 1A4, 2C and 6B1 precipitations using the normal mouse brain homogenates (FIG. 9, lanes 1, 3 and 5) and in the precipitations with 19E probably represent a combination of nonspecific background precipitation of PrP$^{C}$, and the murine IgG light and heavy chains eluted from the magnetic beads that were subsequently detected by goat anti-mouse Ig-HRP conjugate (FIG. 10).

Continued evaluation of the PrP$^{Sc}$-specific monoclonal antibodies revealed that they were capable of recognizing different murine strains of PrP$^{Sc}$ through a conformationally dependent epitope. As depicted in FIG. 11, 1A4 was used in immunoprecipitations on numerous extracts prepared from different mice infected with either the ME7 or 139A strain of murine scrapie. In these experiments, 1A4 was found to specifically precipitate PrP$^{Sc}$ and PrP 27–30, regardless of the strain. This was also found for the other PrP$^{Sc}$-specific monoclonal antibodies (data not shown). When the brain homogenates (normal, ME7 and 139A infected) were electrophoresed in an SDS-PAGE gel under non-reducing conditions and then probed for PrP with one of the PrP$^{Sc}$-specific monoclonal antibodies (1A4 or 6B1) or 6H4, it was clearly evident that only 6H4 was capable of detecting denatured PrP$^{C}$ and PrP$^{Sc}$ (FIG. 12, lanes 7, 8 and 9). For 1A4 and 6B1, the PrP$^{Sc}$-specific determinants had been lost upon denaturation of the sample, establishing the conformational sensitivity of the epitope.

In addition, it was determined that YYR-reactive monoclonal antibodies do not recognize any cell surface proteins on the surface of splenocytes or dissociated immediately ex-vivo brain cells from normal and PrP–/– knockout mice. Viable mouse splenocytes and brain cells were isolated by centrifugation of spleen cell and brain suspensions through a ficol gradient. As shown in FIG. 13, splenocytes were stained with the FITC-conjugated antibodies listed (solid lines), or with isotype-matched FITC labeled control antibodies (dashed lines). Non-viable cells were excluded from the analysis with propidium iodide. The lack of surface immunoreactivity on splenocytes (FIG. 13) or brain cells (not shown) indicates that the YYR conformational epitope is rare, as suggested by the structural searches noted above. Moreover, the lack of appreciable signal provides an acceptable background for studies of PrP$^{Sc}$ immunoreactivity at the cell surface of splenocytes and other test cells. Detection of cell surface PrP$^{Sc}$ is useful as a diagnostic test for human and animal prion disease infection. Finally, the lack of cell surface immunoreactivity provides an independent verification of the fact that anti-YYR antibodies do not recognize PrP$^{C}$, as splenocytes and brain cells possess detectable surface PrP$^{C}$ by 6H4 immunohistochemistry (not shown).

Species specificity of the YYR epitope has also been examined. In studies using brain homogenates from scrapie-infected hamsters, the above-described PrP$^{Sc}$-specific monoclonal and polyclonal antibodies were found to immunoprecipitate hamster PrP$^{Sc}$ (FIG. 14). In addition, similar specificities for PrP$^{Sc}$ and PrP 27–30 that were evident in the studies with infected murine tissues were also observed. For example, monoclonal antibody 1A4 specifically immunoprecipitates PrP$^{Sc}$ and PrP 27–30 (FIG. 14, lanes 3 and 4), whereas the polyclonal goat antibody p165 specifically immunoprecipitates only PrP$^{Sc}$ from infected hamster brains (FIG. 14, lanes 7, 8, 9, and 10). In addition to hamster, PrP$^{Sc}$ from infected sheep, bovine, and human tissues, if desired, may be specifically precipitated using any of the techniques described herein.

Materials and Methods

These PrP$^{Sc}$-specific antibodies described above were obtained and tested using the following materials and methods.

Circular Dichroism

Circular dichroism was performed according to methods described by Hornemann and Glockshuber (*Proc. Natl. Acad. Sci.* 95:6010, 1998). Far-UV circular dichroism spectra were recorded on an Aviv Circular Dichroism Spectrometer model 62DS (Lakewood, N.J.) at 25° C. using quartz cells with a path length of 0.1 cm. Spectra were obtained from 195 nm to 260 nm, with a 1.0 nm step, 1.0 nm bandwidth, and 4-second collection time per step. The experimental data were expressed as mean residue ellipticity (deg θcm$^2$dmol$^{-1}$).

Fluorescence Spectroscopy

Fluorescence spectroscopy was performed according to the methods described in Chin et al. (*Biochemistry* 31:1945–51, 1992).

Preparation of the Immunizing YYR Peptides

In order to develop an antibody to PrP$^{Sc}$, a peptide with the amino acid sequence Acetyl-Cys-Tyr-Tyr-Arg-NH2 (YYR) (SEQ ID NO: 32) was synthesized, conjugated to KLH, and injected intramuscularly into rabbits using well known techniques.

At the amino-terminus of the peptide, a cysteine residue was added to allow conjugation of the peptide with the protein carrier. The amino group of the peptide was blocked by acetylation, and the carboxylic group of the peptide was blocked by amidation.

Peptide Synthesis

Peptides were synthesized using solid phase peptide synthesis methods either manually or automated (MPS396 peptides synthesizer, Advanced ChemTech). Coupling of amino acid residues was accomplished using Fmoc peptide synthesis chemistry (Fields et al., 1990, IJPPR 35, 161). Syntheses were performed on Wang or on amide Rink resins, with full side chain protection of amino acids. Since the alpha-$NH_2$ groups of the amino acids were protected with the Fmoc group, the following protective groups were chosen for the side groups of the trifunctional amino acids:

Cysteine: 5-triphenylmethyl (Trt)
Arginine: 2,2,4,6,7-pentamethyldihydrobenzofuran-5-sulfonyl (Pbf)
Tyrosine: tert.-butyl ether (tBu)

BOP, PyBOP, or TBTU were used as activation agents, depending on the chemistry and difficulty of the coupling reaction. All chemicals were purchased from Advanced ChemTech, Bachem, and Calbiochem/NovaBiochem. Formation of each peptide bond between residues of the sequence was ensured by using a 3 to 6 fold excess of coupling reagents and by so-called double coupling; meaning that the coupling reaction was repeated for each amino acid added to the growing peptide chain.

Cleavage of Fluo-Peptides from Resin

After synthesis, the peptides were cleaved from the resin using the Reagent K as a cleavage mixture: water (2.5%), TIS (2.5%), EDT (2.5%), TFA (92.5%). The peptides were then precipitated with cold diethyl ether. The precipitates were centrifuged, washed three times with diethyl ether, dissolved in 20%–50% AcCN/water mixture, and lyophilized. Analysis of crude products was performed using analytical RP-HPLC and electrospray MS.

HPLC Purification

The crude peptide was purified by RP-HPLC (reverse phase high performance liquid chromatography) on a Vydac C18 column, 2.5×25 cm, using a linear gradient of 10–50% acetonitrile in water, with 0.06% TFA (1%/min gradient, 10 ml/min flow rate), with monitoring by UV at 215 nm and 254 nm. Analytical HPLC was used to estimate the purity of the fractions. The final product was obtained as a lyophilized peptide with at least 95% purity estimated by analytical HPLC (Vydac C18, 0.46×25 cm, linear gradient 10–60% acetonitrile in water, 0.1% TFA, 1%/min, 1 ml/min flow rate, detection by UV absorption at 215 nm and 254 nm). The pure peptide was identified by molecular mass analysis using a SCIEX API III mass spectrometer according to standard procedures.

Analytical Data

The retention time of the peptide on RP-HPLC was 21.215 minutes. The theoretical molecular weight of the peptide was calculated to be 644.74; the actual molecular weight, through molecular mass analysis, was found to be 646.5 (MW+$H^+$).

Coupling of the Peptide to a Carrier

Peptides were coupled to a carrier, in this case keyhole limpet hemocyanin (KLH). Other carriers useful for such coupling include, without limitation, albumin, or ovalbumin, 8map, or lysozyme. Coupling was effected via a thioether linkage to the mercapto group of the cysteine. This type of linkage has the advantage that the peptide is coupled in a defined way to a carrier protein.

Coupling to KLH was performed as follows. 10 mg of the peptide was dissolved in 2 ml of phosphate buffered solution (PBS 1×). 1 ml of KLH (Pierce products #77100) was added to the peptide solution and stirred (1 mole of peptide/50 amino acids). The KLH concentration was 10 mg/ml. 20 µl of glutaraldehyde (25% aqueous solution) was added to the peptide/carrier solution with constant stirring, incubated for 1 hour, after which a glycine stop solution was added. The peptide/carrier conjugate was separated from the peptide by dialysis against PBS.

Additional YYR peptides (e.g., CYYRRYYRYY (SEQ ID NO: 33) and CKYEDRYYRE (SEQ ID NO: 34)) were synthesized according to standard methods, for example, those described herein. Other synthetic peptides can be prepared by making appropriate modifications of the above-described synthetic methods. Such peptides are also characterized using any of the standard methods known in the art (e.g., those described herein).

Immunization of Rabbits

Polyclonal antibodies were prepared according to standard methods, and an immune response was enhanced with repeated booster injections, at intervals of 3 to 8 weeks. The success of the immunization was verified by determining the concentration of antibodies in a western blot or ELISA or both. More specifically, to generate polyclonal antibodies to $PrP^{Sc}$, the tripeptide YYR conjugated to KLH was injected into rabbits in accordance with a 164 day immunization regimen, after which the animals that had produced specific antibodies were bled.

In order to sample the serum prior to immunization, 10 ml of blood per rabbit was taken as a preimmune control. Primary immunizations were carried out with Freund's complete adjuvant and subsequent boosts with incomplete Freund's adjuvant (IFA) (1 ml per rabbit, 0.5 ml per thigh muscle). Each injection consisted of approximately 200 µg of the purified peptide. At days 21, 42, and 70, a booster injection was given with IFA. At days 31, 42 and 80, 10 ml of blood was collected from the central ear artery for titer determination (6 ml/kg/rabbit). At day 80, the titer of the sera was checked, and 3 more injections were given (IFA) at 4 week intervals, followed by blood sampling 10 days later. 10 days after the last boost, anesthetized rabbits were exsanguinated via cardiac puncture, and antisera was collected.

Immunization of Goats

Goat polyclonal antibodies were generated according to standard methods. Three goats were immunized as follows. On day 1, all the goats received a primary immunization of 1 mg of YYR-KLH conjugates in complete Freund's adjuvant. Boosts were done by injection of 1 mg YYR-KLH in incomplete Freund's adjuvant for two of the three goats, whereas the third goat received 1 mg YYR-8map conjugates in incomplete Freund's adjuvant. Serum samples from each of the three bleeds were tested for reactivity by ELISA against YYR-BSA conjugates. From the third set of bleeds, total IgG was purified by ammonium sulfate precipitation and YYR-reactive IgG was purified using a YYR affinity column. IgG fractions were tested for reactivity to $PrP^{Sc}$ as described herein. The exact immunization schedule was as follows: Day 1, primary immunization; Day 21, first boost immunization; Day 30, first bleed; Day 46, second boost immunization; Day 53, second boost immunization; Day 60, second bleed; Day 76, third boost immunization; Day 83, third boost immunization; and Day 90, third bleed.

Alternatively, monoclonal antibodies may be prepared using the synthetic peptides described herein and standard hybridoma technology (see, e.g., Kohler et al., Nature 256, 1975; Kohler et al., Eur. J. Immunol. 6:511, 1976; Kohler et al., Eur. J. Immunol. 6:292, 1976; Hammerling et al., In

*Monoclonal Antibodies and T Cell Hydridomas*, Elsevier, NY, 1981; Ausubel et al., 1999, *Current Protocols in Molecular Biology*, Wiley Interscience, New York,). Once produced, monoclonal antibodies are also tested for specific PrP recognition by immunoprecipitation and western blot analysis (e.g., by using the methods described in Ausubel et al., supra).

Immunization of Mice

The generation of monoclonal antibodies was carried out as follows. Mice were immunized with baculovirus supernatant containing mouse PrP-AP fusion protein in complete Freund's adjuvant, then boosted 2 weeks later with the same antigen in incomplete Freund's adjuvant. Two weeks after that immunization the mice were boosted with a mixture of PrP-AP supernatant plus 100 µg of KLH-CYYRRYYRYY and 100 µg of KLH-CKYEDRYYRE conjugates. Splenocytes from these mice were fused to the FO murine B cell line (ATCC CRL-1646) to generate specific hybridoma clones. Hybridoma supernantants were screened by ELISA. There were no reactive supernatants to PrP-AP or to the CKYEDRYYRE sequence, although there were clones reactive to YYR-8map conjugates.

Purification of Antibody

Total rabbit IgG was purified from serum using the Pharmacia protein A HiTrap column according to the manufacturer's recommendations. Briefly, a HiTrap column was equilibrated with 3 column volumes of start buffer (0.2M sodium phosphate buffer, pH 7.0). Serum was applied, using a syringe through a luer adaptor, onto the column. The column was subsequently washed with 5 ml of start buffer. Bound protein was eluted with 0.1M glycine, pH 3.0, and collected in eppendorf tubes containing 1M Tris pH 8.0 (50 µl/500 µl sample). Fractions were analyzed on SDS-PAGE.

Goat polyclonal antibodies were purified from serum samples as is described above.

Mouse monoclonal antibodies were produced as ascites, and purified using a protein A column kit (Pierce) according to the manufacturer's instructions. Briefly, a sample of ascites was diluted with binding buffer at a 1:1 final ratio. The sample was then added to the top of the column, which had been previously equilibrated with binding buffer, and allowed to flow through the matrix. The pass-through material was collected and the column washed with 5 volumes of binding buffer. Mild elution buffer was added to the column to release the bound IgG antibody from the matrix. Other antibody isotypes were collected by switching to the IgG elution buffer. All the antibodies were collected in 1 ml fractions, which were analyzed by BCA to determine total protein content and SDS-PAGE electrophoresis to establish the degree of antibody purity. The fraction containing the most yield of IgG was desalted by passing it through a D-salt column (Pierce). The antibody fraction was allocated and stored at −80° C. in PBS.

Antibodies produced using the afore-mentioned procedures were subsequently tested for high-affinity binding as follows.

Preparation of Bovine Brain Homogenates

Two methods were used for the preparation of bovine brain homogenates. In one method (A), brain samples were homogenized in tissue homogenization buffer (10% sucrose, 20 mM HEPES pH 7.5, 2% Sarcosyl, and 5 mM EDTA) using a Polytron (OMNI GLH). Homogenates were used at a final concentration of 1% (w/v). In a second method (B), brain homogenate was prepared as a 10% (w/v) solution. Bovine brain was disrupted in a Dounce homogenizer (with a Teflon pestle) in 2 volumes of cold lysis buffer (100 mM NaCl, 10 mM EDTA, 0.5% Nonidet P-40, 0.5% sodium deoxycholate in tris-HCl, pH 7.4). The sample was incubated on ice for 20 minutes before applying 15 additional strokes in the homogenizer. Cellular debris was removed by centrifugation at 3000 rpm for 15 minutes at 4° C. The protein content of the supernatant was subsequently quantitated.

Preparation of Hamster and Mouse Homogenates

Hamster or mouse brain tissue was added to enough homogenization buffer (PBS 0.5% NP40, 0.5% deoxycholate) to result in an 10% (weight/volume) homogenate. The tissue was homogenized by being repeatedly passed through an 18 gauge needle and a 22 gauge needle. Cellular debris was removed by two sequential centrifugations at 500 g for 20 minutes. The total protein in the supernatant was quantitated with the BCA kit (Pierce), and the concentration was adjusted using homogenization buffer to a final concentration of 5 mg/ml. Aliquots containing 200 µl each were prepared and stored at −80° C.

Magnetic Bead Conjugation

Sixty to 150 µg of purified antibody or BSA were conjugated to approximately $6 \times 10^8$ tosylactivated magnetic beads (Dynal) using a protocol supplied by the manufacturer. Briefly, 1 ml of homogeneous unconjugated bead suspension per antibody was washed twice and resuspended in PBS pH 7.4 containing the antibodies or the BSA. The mixture was incubated at 37° C. for 20–24 hours on a rotor. The mixture was then washed twice for 5 minutes with rotation in PBS 0.1% BSA and incubated in blocking buffer (0.2 M Tris pH 8.5 0.1% BSA) for 4 hours at 37° C. with rotation. Following another 5 minute wash with PBS 0.1% BSA, the antibody-bead conjugates were washed in PBS 0.1% BSA 1% Tween-20 for 10 minutes, washed again with PBS 0.1% BSA and stored at 4° C.

Proteinase K Digestion

Bovine brain homogenate was incubated with proteinase K solution (100 µg/ml) at 50° C. for 30 minutes. The digestion was stopped with the protease inhibitor, PMSF (2 mM).

Mouse and hamster brain homogenates were digested with 45 µg/ml final concentration Proteinase K for 30 minutes at 37° C. The reaction was stopped with the addition of 19 mM PMSF final concentration.

Immunoprecipitation

Ten µl of brain extract was added to 950 µl of immunoprecipitation buffer (PBS 3% NP-40, 3% Tween-20) and incubated at 37° C. for 30 or 60 minutes. For experiments evaluating the reactivity of PrP 27–30 with the bead conjugates, the incubation was preceded by addition of 50 µl of 1 mg/ml proteinase K. Samples not treated with proteinase K were still incubated at 37° C. for the appropriate time period. After the incubation, 60 µl of an 100 mM PMSF solution were added to both sets of tubes. One hundred µl of resuspended bead conjugates were then added to the mixture, and incubated with rotation at room temperature for 2 hours. The beads were washed 3 times with washing buffer (PBS 2% NP-40 2% Tween-20) and resuspended by vortex after each wash. After the last wash, the beads were resuspended in 20 µl of 2× loading buffer (100 mM Tris pH 6.8, 4% SDS, 0.015% bromphenol blue, 20% glycerol) and heated at 95° C. for 3 minutes.

Western Blot

The PrP$^{Sc}$ content of brain homogenates was determined by western blotting according to standard methods. Protein samples were mixed with 2× sample buffer at a ratio of 1:1 and boiled for 5 minutes at 100° C. SDS-PAGE analysis was performed according standard methods. Samples were applied to a pre-cast 15% acrylamide gels (Biorad) along with pre-stained molecular weight markers (Biorad). The gels were run at 100V until the bromophenol blue dye front reached the bottom of the gel. The separated protein was then transferred onto PVDF membranes at 100 V for 1 hr. The membrane was blocked for 30 minutes in blocking buffer, after which it was washed three times with TBST. The membranes were then incubated with an antibody specific for denatured PrP for 2 hours at room temperature. The membranes were washed as described above before incubation with a goat anti-mouse IgG alkaline phosphatase conjugated secondary antibody (1:5000 in TBST) for 1 hour at room temperature. After washing, signals were developed with the chemiluminescent substrate CDP-star, and exposed to X-ray films.

Flow Cytometry

Spleen cell suspensions were prepared from Balb/c mice by passing the tissues through a wire mesh. The cells were washed once with cold Dulbecco's PBS without $Ca^{2+}$ or $Mg^{2+}$ and viable cells were isolated by underlayering of the cell suspension with Lympholyte (Cedarlane) and centrifugation at 1300 g for 20 minutes. The cells were washed once with cold Dulbecco's PBS without $Ca^{2+}$ or $Mg^{2+}$2.5% fetal bovine serum, and $0.5 \times 10^6$ cells were aliquoted per well in a round bottom 96 well plate. The cells were centrifuged and resuspended in 50 μl of antibody-FITC conjugates at $\frac{1}{10}$ final concentration in Dulbecco's PBS without $Ca^{2+}$ or $Mg^{2+}$2.5% fetal bovine serum, for 15 minutes on ice. The cells were then washed twice with cold Dulbecco's PBS without $Ca^{2+}$ or $Mg^{2+}$2.5% fetal bovine serum and resuspended in the same medium containing 1 μg/ml of propidium iodide. The cells were analyzed on a Coulter Epics flow cytometer and were gated by size and granularity (forward and side scatter) and viability (exclusion of propidium iodide fluorescence).

FITC Antibody Conjugation

Fluoresceinated mAbs were made by using the Fluorotag kit (Sigma) following the manufacturer's instructions. Briefly, 0.5 mg of each antibody was raised to pH 9 with concentrated bicarbonate buffer, and FITC stock solution was added to produce an FITC: antibody ratio of 20:1. The vials were then incubated for 2 hours at room temperature. Labeled antibody was separated from free FITC by passing the mixture over a Sephadex G-25M column. Conjugated antibodies were tested for successful fluoresceination by measuring their FITC emissions at 535 nm using an LJL Biosystems Analyst, and the antibodies were tested for retention of their binding activity with an ELISA against YYR-8map conjugates.

Determination of PrP Content of the Brain Homogenates

The presence of both PrP$^C$ and PrP$^{Sc}$ in extracts prepared from brain samples was confirmed by Western blotting using mAb6H4 (FIG. 3). The dispersed banding pattern of PrP$^C$ (33–35 kDa) was observed in extracts prepared from both normal and BSE-infected brain samples. After treatment of the extracts with proteinase K, PrP$^C$ was digested completely, whereas PrP$^{Sc}$ appeared as a 27–30 kDa band.

All brains were characterized for the presence of PrP$^{Sc}$, which accounted for 15–20% of the total PrP content in the pooled extracts (FIG. 15).

Soluble Protocadherin-2 (sPC2) Expression

PC2, a PrP binding protein, was used as a capture reagent for PrP$^C$ and PrP$^{Sc}$ to demonstrate PrP$^{Sc}$ specificity of pAbC2. A plasmid (HU-PC43 3'trunc/PC1nel) containing the human protocadherin-2 sequence coding for all six cadherin domains, but truncated at the start of the transmembrane domain, was transfected into COS cells. The culture medium containing the soluble form of protocadherin-2 was collected, and the presence of sPC2 was determined by western blotting using an anti-PC2 monoclonal antibody. WO 97/45746, entitled, "Prion Protein Binding Proteins and Uses Thereof," describes the use of PC2 as a receptor for the prion protein, and is hereby incorporated by reference.

Testing of pAbC2 in an ELISA

To determine whether pAbC2 was useful in specifically recognizing PrP$^{Sc}$ from bovine brain extracts, compared to PrP$^C$ using recombinant PrP (rbPrP), an ELISA approach was used. Either pools of PrP$^{Sc}$-containing brain extracts or rbPrP was used to test the specificity of pAbC2 for PrP$^{Sc}$.

The wells of an Immunolon ELISA plate (Dynex) were coated overnight at 4° C. with the PC2-containing culture supernatant in a TBS buffer containing 50 mM Tris, pH 7.5, 150 mM NaCl, 1 mM $CaCl_2$. For BSE-brain extract experiments, control wells were coated with a supernatant containing Mek-4; for rbPrP experiments, milk was used as a control to determine the non-specific binding of the antibody to the well. The coating of the ELISA plates with soluble PC2 was confirmed with an anti-PC2 monoclonal antibody. The wells were washed four times using a SLT 'Columbus' microplate washer (Tecan) with TBS containing 0.05% Tween 20, and blocked by filling the wells with 0.2% I-Block (Tropix) in TBST and incubating the plate at 37° C. for 1 hour. The plates were washed and the bovine brain homogenate (diluted to 1% w/v in TBS) or rbPrP was added to designated wells and incubated at RT for 1 h. Wells were washed four times with TBST. pAbC2 was added to appropriate wells and incubated at RT for 1 hour, followed by a further 45 minute incubation with 100 μl of an anti-rabbit or mouse IgG/horseradish peroxidase conjugate (1:5000) in TBST containing 1% nonfat milk. Wells were washed four times with TBST. Signals were developed with TMB/$H_2O_2$ as a substrate for peroxidase. Reactions were stopped after 15 minutes by the addition of 100 μl of 2 M phosphoric acid. Signals were monitored at 450 nm with reference at 620 nm using a SLT microplate reader. Specific positive signals were determined by comparing PrP binding to PC2 with PrP binding to the negative control, Mek-4 or milk. Preimmune controls showed no binding.

In all cases of BSE-infected bovine brain extracts, the recorded absolute values for these points were higher than the recordings for the extracts from normal brain, regardless of the presence of sPC2 on the plates. It is conceivable that aggregation in the BSE samples resulted in nonspecific adherence to wells of the ELISA plates, hence, higher signals were recorded. However, values for BSE samples nonetheless were greater than those obtained in the same samples probed with the Mek-4 control.

The pAbC2 reacted more strongly to PC2-bound material than to Mek4-bound material, often 1.5–2 times greater than binding to Mek-4 control, suggesting specific binding to PrP$^{Sc}$ (FIG. 16). pAbC2 antibody as a secondary detection reagent bound only to PrP$^{Sc}$-positive samples in most cases, suggesting that this combination of reagents may enable PrP$^{Sc}$ detection in the absence of a protease pre-treatment.

PrP Detection Assay Using Immunoprecipitation

Once it was established that pAbC2 recognized PrP$^{Sc}$ in the ELISA assays, an immunoprecipitation was subsequently done to verify whether pAbC2 could immunoprecipitate PrP from bovine brain extracts. Pools of several normal or BSE-infected brain extracts were used in the experiments, unless indicated otherwise. All brain samples had previously been characterized for the presence of PrP$^{Sc}$. Briefly, 20 μl of a 10% brain homogenate was incubated for 2 h at RT with various antibodies that are known to bind to PrP, such as mAb6H4, as well as pAbC2 in TBS containing 0.5M GuHCl. After incubation with 25 μl of magnetic protein A- or protein G-coupled beads (Dyna-beads) for 1 hour at room temperature, agarose beads were pelleted using a magnet. Pellets were washed three times and then boiled in SDS-sample buffer for analysis on western blots. PrP was detected with an anti PrP polyclonal or monoclonal antibody.

Using pAbC2, PrP was not detected in reactions containing extracts from normal brain, however, bands migrating at a position similar to PrP were detected in reactions containing extracts from BSE-infected samples (FIG. 7). These results further substantiated the ELISA studies showing that pAbC2 is specific for PrP$^{Sc}$, and not for PrP$^C$. Uncoupled beads were used as a negative control, and showed no precipitation of PrP$^{Sc}$. mAb 6H4 was used as a positive control in the immunoprecipitation reactions. As expected, PrP$^C$ was efficiently precipitated from normal brain using mAb 6H4.

Use

The PrP peptides and PrP$^{Sc}$-specific antibodies described herein may be used, for example, for the following diagnostic, therapeutic, vaccine, and decontamination purposes, as well as for screening for novel compounds that can be utilized to diagnose or combat prion diseases or decontaminate prion samples.

Test Kits for the Diagnosis of Prion Diseases

Epitope-specific anti-PrP antibodies find diagnostic use generally in the detection or monitoring of prion diseases. For example, anti-PrP antibodies may be used to monitor the presence or absence of $PrP^{Sc}$ in a biological sample (e.g., a tissue biopsy, a cell, or fluid) using standard detection assays. Immunological assays may involve direct detection of $PrP^{Sc}$, and are particularly suited for screening large amounts of samples for the presence of $PrP^{Sc}$. For example, polyclonal or monoclonal antibodies produced against a continuous YYX epitope such as YYR (as described above) may be used in any standard immunoassay format (e.g., ELISA, Western blot, immunoprecipitation, flow cytometry, or RIA assay) to measure complex formation. In addition, if desired, because of the specificity of the antibodies described herein for $PrP^{Sc}$, pretreatment of a test sample with protease prior to immunological analysis may be omitted. Any appropriate label which may be directly or indirectly visualized may be utilized in these detection assays including, without limitation, any radioactive, fluorescent, chromogenic (e.g., alkaline phosphatase or horseradish peroxidase), or chemiluminescent label, or a hapten (for example, digoxigenin or biotin) which may be visualized using a labeled, hapten-specific antibody or other binding partner (e.g., avidin). Exemplary immunoassays are described, e.g., in Ausubel et al., supra, Harlow and Lane, *Antibodies: A Laboratory Approach, Cold Spring Harbor Laboratory, New York* (1988), and Moynagh and Schimmel, *Nature* 400:105, 1999. For example, using the antibodies described herein, $PrP^{Sc}$ is readily detected at the cell surface (e.g., a leukocyte) using standard flow cytometry methods such as those described herein. Samples found to contain increased levels of labeled complex compared to appropriate control samples are taken as indicating the presence of $PrP^{Sc}$, and are thus indicative of a prion-related disease.

In addition, novel compounds useful for diagnosing prion disease may be identified using the antibodies of the invention. For example, combinatorial chemical libraries or small molecule libraries are screened to identify compounds having the ability to inhibit the binding interaction of one or more anti-YYX antibodies to a YYX epitope according to standard methods (e.g., equilibrium dialysis, Biacore analysis, or competitive inhibition). Such libraries may be derived from natural products, synthetic (or semi-synthetic) extracts, or chemical libraries according to methods known in the art. Those skilled in the field of drug discovery and development will understand that the precise source of compounds is not critical to the screening procedure(s) of the invention. Examples of natural compound sources include, but are not limited to, plant, fungal, prokaryotic, or animal sources, as well as modification of existing compounds. Numerous methods are also available for generating random or directed synthesis (e.g., semi-synthesis or total synthesis) of any number of chemical compounds, including, but not limited to, saccharide-, lipid-, peptide-, and nucleic acid-based compounds. Synthetic compound libraries may be obtained commercially or may be produced according to methods known in the art. Furthermore, if desired, any library or compound is readily modified using standard chemical, physical, or biochemical methods.

Compounds that inhibit binding of an anti-YYX antibody to an YYX epitope at lowest concentration are referred to as "high affinity competitors" and are useful in the diagnotic methods of the invention. Such high affinity competitors that mimic the activity of the anti-YYX antibody (for example, the complementarity determining region ("CDR") of an anti-YYX antibody) are subsequently tested for efficient recognition and binding of $PrP^{Sc}$. Once identified, high affinity competitors may be coupled to solid substrates (for example, ELISA wells or beads) for use in the capture phase of virtually any diagnostic test for prion infection.

Conversion of Anti-$PrP^{Sc}$ Monoclonal Antibody to IgM

Diagnostic methods may also be carried out using IgM antibodies, which have increased avidity for $PrP^{Sc}$. In order to increase antibody avidity for $PrP^{Sc}$, a specific binding IgG Fab region gene may be constructed into a pentavalent IgM fragment as follows.

Immunoglobulin (Ig) molecules are composed of distinct structural and functional domains. Each immunoglobulin is made up of 2 heavy chains (50–80 kD each) and 2 light chains (25 kD each). The heavy chains are a product of the rearrangement of one of four types of immunoglobulin genes, the $V_H$, $D_H$, $J_H$ and $C_H$. The first three genes, collectively known as the variable region, combine to create the binding site of the heavy chain. The fourth gene, $C_H$, also known as the constant region, is not involved in the generation of the binding site but contributes to the heavy chain's recognition by other components of the immune system. Similarly, the light chain is derived from the rearrangement of one copy of 3 types of immunoglobulin genes, the $V_L$, $J_L$, and $C_L$. As for the heavy chain, the binding site of the light chain is generated by the combination of the $V_L$ and $J_L$ genes, whereas the $C_L$ gene is not involved. The binding site of any given antibody is thus produced by the interaction of two variable regions: the $V_H$-$D_H$-$J_H$ polypeptide and the $V_L$-$J_L$ polypeptide. Most antibodies have two such binding sites.

During an immune response the first type of immunoglobulin made is called IgM. Generally IgMs contain binding sites with relatively low affinities, but compensate for that characteristic by expressing five binding sites per antibody molecule. As the immune response progresses, other antibodies such as IgGs are generated, which contain much higher affinities than the IgMs that came before, but only two binding sites per molecule.

As noted above, the tripeptide YYR or related motifs appear three times in the PrP sequence. In bovine, rodent and human PrP the motif appears twice as YYR and once as YYX. It is possible, therefore, as more of these individual motifs are detected by a particular reagent, the more sensitive that reagent will be. The highest affinity binding sites are contained within IgG molecules. However, as they only have two binding sites, these antibodies may not be the optimum reagents for detection of $PrP^{Sc}$. IgM molecules contain enough binding sites, but they are of lower affinity, therefore they are not the optimum reagents for detection of $PrP^{Sc}$. Modular construction of an Ig molecule therefore provides a solution to this problem, and a way to construct an optimum Ig for the detection of $PrP^{Sc}$.

The YYR-KLH antigen that was used to generate the anti-PrP$^{Sc}$ polyclonal antibody is used to immunize mice. The mice are immunized using protocols established in the field that are known to result in high affinity IgG antibodies. B cell hybridomas are generated by standard procedures, and tissue culture supernatants generated from these cells that contain their secreted monoclonal antibodies are tested for immunoreactivity to the YYR moiety of the antigen by ELISA. The rearranged immunoglobulin genes that produce the antibody are cloned using a one-sided PCR protocol as described in Heinrichs et al. (*J. Immunol. Methods,* 178: 241–51, 1995). Only the variable regions of the heavy and light chains need to be cloned. These are then inserted, using standard procedures, into expression vector plasmids containing an appropriate constant region, in this case, the secretory version of an IgM constant region, but could be any other Ig isotype. This region may be obtained either from mouse or human origin, the latter to humanize the antibody such that it results in minimal side effects after administration to humans (for reviews see Winter and Harris, *Immunol Today,* 14(6):243–6, 1993; Vaughan et al., *Nature Biotech,* 16(6):535–9, 1998). The vectors, which now contain variable regions derived from IgG molecules coupled to constant regions derived, e.g., from IgM molecules, are then used to drive the generation of recombinant anti-PrP$^{Sc}$ antibodies either in bacterial or eukaryotic expression systems. For an example of such a strategy see Poul et al., *Immunotechnology,* 1:189–96, 1995.

Alternatively, the variable region combination yielding the best reactivity against the YYR moiety of the YYR-KLH antigen will be selected from a phage display library as described in the literature (Marks et al., *J. Mol. Biol,* 222:581–597, 1991; Vaughan et al., *Nature Biotech,* 14:309–14, 1996) before undergoing the isolation and subcloning into a full length antibody described above.

Conversion of Anti-PrP$^{Sc}$ Monoclonal Antibody to IgE

An alternative method to detect PrP$^{Sc}$ in a sample (e.g., a blood sample) involves the conversion of PrP$^{Sc}$ monoclonal antibody to IgE. PrP$^{Sc}$ forms aggregates of various sizes that normally are not made with PrP$^C$. These PrP$^{Sc}$ multimers may exist in blood of infected individuals. This characteristic may be used to detect PrP$^{Sc}$ with a bioassay. Specifically, monoclonal antibodies that are either specific for PrP$^{Sc}$, or that are cross reactive with PrP$^C$ and PrP$^{Sc}$ are converted, by subcloning, into the IgE isotype. This would involve the same methods as described above, using an IgE constant region instead of an IgM constant region.

IgE antibodies are bound by cell surface receptors specific to the IgE constant region. These receptors are widely distributed in the body and play a central role in allergic reactions. The receptor under consideration here, the high-affinity receptor for IgE (Fc RI), is found on mast cells, basophils, eosinophiles, monocytes and Langerhans cells. It is a cell surface receptor composed of 3 polypeptide chains, and displays an exquisite affinity for IgE ($K_a$=10$^{-10\,M}$). Each Fc RI binds one molecule of IgE (Kulczycki and Metzger, *J. Exp. Med.,* 140:1676, 1974; Barclay et al., *The Leukocyte Antigen Factsbook*, San Diego: Academic Press, 1997). However, in order for a signaling response to be initiated, multiple Fc RI receptors are crosslinked by a multivalent antigen (Metzger, *J. Immunol,* 149:1477, 1992). The intracellular signal intensity is proportional to the degree of cross linkage. Once this occurs, the cell expressing the Fc RI degranulates, causing a rapid release of histamines and other stored mediators.

In the present bioassay method, a blood sample is incubated with a monoclonal antibody reactive to PrP$^{Sc}$, or cross reactive with PrP$^C$ and PrP$^{Sc}$. Monomeric PrP and polymeric PrP (e.g., PrP$^{Sc}$ aggregates) is bound, and the mixture is then incubated with a cell line expressing Fc RI, such as RBL-2H3, known to express 2–3×10$^5$ Fc RI per cell (Barsumian et al., *Eur. J. Immunol,* 11:317, 1981). Such a cell line is available from ATCC. Since aggregation of the Fc RI is required for degranulation to occur, monomeric PrP, whether bound by the antibody or not, will not cause cellular degranulation, however, polymeric PrP will. The released mediators are detected directly in a standard immunological assay, e.g., by ELISA.

PrP$^{Sc}$ Vaccines

Peptides of the invention and mixtures and combinations thereof are also useful as active components of vaccines capable of inducing a prophylactic or therapeutic immune response against prion diseases in hosts susceptible to and/or harboring infection. Routes of administration, antigen doses, number and frequency of injections will vary from species to species and may parallel those currently being used in the clinic and/or experimentally to provide immunity or therapy against other infectious diseases or cancer. For example, the vaccines are pharmaceutically acceptable compositions containing the peptide of this invention, its analogues or mixtures or combinations thereof, in an amount effective in the mammal, including a human, treated with that composition to raise immunity sufficient to protect the treated mammal from prion infection for a period of time. It is also possible that PrP$^{Sc}$-specific immunity prompted by immunization with YYX (YYR, or YYD, or YYQ) or related compounds are useful to favor the degradation of PrP$^{Sc}$ or alleviate manifestations of the disease without affecting the expression or function of PrP$^C$ in the brain and other tissues, resulting in improvement of clinical status in clinically symptomatic humans with prion disease.

Different types of vaccines can be developed according to standard procedures known in the art. For example, a vaccine may be peptide-based, nucleic acid-based, bacterial- or viral-based vaccines. More specifically, with regard to peptide vaccines, peptides corresponding to the PrP$^{Sc}$-specific epitope or a functional derivatives thereof can be utilized as a prophylactic or therapeutic vaccine in a number of ways, including: 1) as monomers or multimers of the same sequence, 2) combined contiguously or non-contiguously with additional sequences that may facilitate aggregation, promote presentation or processing of the epitope (e.g., class I/II targeting sequences) and/or additional antibody, T helper or CTL epitopes to increase the immunogenicity of the PrP$^{Sc}$-specific epitope as a means to enhance efficacy of the vaccine, 3) chemically modified or conjugated to agents that would increase the immunogenicity or delivery of the vaccine (e.g., fatty acid or acyl chains, KLH, tetanus toxoid, cholera toxin, etc.), 4) any combination of the above, 5) the above in combination with adjuvants, including but not limited to aluminum salts, saponins or triterpenes, MPL, and cholera toxin, and/or delivery vehicles, including but not limited to liposomes, VPLs or virus-like particles, microemulsions, attenuated or killed bacterial and viral vectors, and degradable microspheres, 6) administered by any route or as a means to load cells with antigen ex vivo.

Examples of uses of nucleic-acid based vaccines as a prophylactic or a therapeutic include: 1) any nucleic acid encoding the expression (transcription and/or translation) of the PrP$^{Sc}$-specific epitope, 2) additional nucleic acid sequences that facilitate processing and presentation, aggregation, secretion, targeting (to a particular cell type) of the PrP$^{Sc}$-specific epitope, either translational fusions or independent transcriptional units, 3) additional nucleic acid sequences that function as adjuvants/immunomodulators, either translational fusions or independent transcriptional units, 4) additional antibody, T helper or CTL epitopes that increase the immunogenicity of the PrP$^{Sc}$-specific epitope or efficacy of the vaccine, either translational fusions or independent, 5) any combination of the above, 6) the above administered in saline ('naked' DNA) or in combination with an adjuvant(s), (e.g. aluminum salts, QS-21, MPL), immunomodulatory agent(s) (e.g. rIL-2, rGM-CSF, rIL-12), and/or nucleic acid delivery agents (e.g. polymer-, lipid-, peptide-based, degradable particles, microemulsions, VPLs, attenuated bacterial or viral vectors) using any route or ex vivo loading.

Attenuated or killed bacterial or viral vectors can be used to deliver either the antigen or DNA/RNA that codes for the expression of the antigen. These can also be used as a means to load cells with antigen ex vivo.

Vaccines are prepared according to standard methods known in the art, and will be readily applicable to any new or improved method for vaccine production.

Prion Decontamination

The methods and compositions described herein are useful for the decontamination of biological samples that are known or suspected of being contaminated with a prion, e.g. intended for transplantation. In particular, biological samples may be incubated with anti-PrP$^{Sc}$ antibody, and the complexes removed using standard methods. Alternatively, anti-PrP$^{Sc}$ antibodies may be incubated with biological samples to complex with, and thereby inhibit the infectivity of prion.

Prion Disease Therapeutics

The methods and compositions of the invention also provide a means for treating or preventing prion diseases in mammals including, without limitation, humans, sheep, pigs, cattle, goats, dogs, cats, and pet species. As noted above, it is possible that changes in the orientation of tyrosine side chains in the tyrosine dimers, or clustering of YYX epitopes (e.g., YYR/D/Q) might contribute to the change in physicochemical properties of PrP upon conversion to PrP$^{Sc}$, such as hydrophobicity and tendency to aggregate. It is also possible that these residues might be critical in the PrP$^C$ to PrP$^{Sc}$ conversion reaction. If this can be shown, then treatments for prion diseases can be based upon antagonists that disrupt, suppress, attenuate, or neutralize the biological events associated with PrP$^C$ to PrP$^{Sc}$ conversion. Antibodies actively produced from YYX (e.g., YYR) peptide immunization, or passive transfer of polyclonal or monoclonal antibodies against YYX, are useful in treating these diseases. Moreover, the invention includes not only an intact monoclonal antibody, but also an immunologically active antibody fragment. Examples of such a fragment include a Fab or (Fab)$_2$ fragment, an engineered single chain F$_v$ molecule, and a chimeric antibody (such as a "humanized" antibody). The term "humanized antibody," as used herein, refers to antibody molecules in which the amino acid sequence in the non-antigen binding regions has been altered so that the antibody more closely resembles a human antibody, and still retains its original binding ability. Humanized forms of non-human (e.g., murine) antibodies are constructed and characterized according to standard methods known in the art, for example, those described in Kutemeier et al. (*Biotechniques* 17:242–246, 1994); Major et al. (*Hum. Antibodies Hybridomas* 5:9–17, 1994); Jolliffe (*Int. Rev. Immunol.* 10:241–250, 1993); Carter et al. (*Biotechnology* 10: 163–167, 1992); Miyachi et al. (*J. Clin. Lab. Anal.* 6:343–50); and Leung et al. (*Mol. Immunol.* 32:1413–1427, 1995). Humanized antibodies are less likely to be immunogenic and are useful in passive immunotherapies. Furthermore, a chimeric antibody of the invention may, if desired, include a variable region of a non-human antibody, e.g., a murine variable region, and a constant region of a human antibody. In some embodiments of the invention, an antibody or antibody fragment is linked to a detectable label. Examples of detectable labels include a radioactive label, a non-radioactive isotopic label, a fluorescent label, an enzyme label, and a colorimetric label.

Moreover, small molecules derived from the structure of the YYR epitope(s), including but not limited to tyrosine side-chain derivatives, may block the conversion reaction. Finally, direct chemical modification of critical residues, such as enzymatic lysis of tyrosine rings, or covalent derivatization of tyrosine rings with bulky substitutions, may also disrupt the PrP$^C$ to PrP$^{Sc}$ conversion reaction if amino acids in the YYR epitope(s) prove to be critical in the conversion process.

For example, such compounds may be identified using the antibodies of the invention. Accordingly, combinatorial libraries or small molecule libraries or both (infra) are screened to identify compounds having the ability to inhibit the binding interaction one or more anti-YYX antibodies to a YYX epitope according to standard methods (e.g. equilibrium dialysis, Biacore analysis, or competitive inhibition). Compounds that inhibit binding of such an antibody are useful in the therapeutic methods of the invention. Once identified, such compounds are tested for their ability to combat prion diseases in any appropriate model system.

Evaluation of whether a test antagonist confers protection against the development of a prion disease in vivo generally involves using an animal known to develop such a disease (e.g., Chandler, *Lancet* 6:1378–1379, 1961; Eklund et al., *J. Infectious Disease* 117:15–22, 1967; Field, *Brit. J. Exp. Path.* 8:129–239, 1969). An appropriate animal (for example, a mouse or hamster) is treated with the test compound according to standard methods, and a reduced incidence or delayed onset or progression of a prion-related illness, compared to untreated control animals, is detected as an indication of protection. The test compound may be administered to an animal which has previously been injected with a prion agent or, alternatively, the test compound may be tested for its ability to neutralize a prion agent by pre-incubating the prion and the compound and injecting the prion/compound mixture into the test animal. A molecule (e.g., an antagonist as described above) that is used to treat or prevent a prion disease is referred to as an "anti-prion therapeutic."

Alternatively, it is possible that circulating antibodies reactive against PrP$^{Sc}$ may act to accelerate the disease by stabilizing the conformation of PrP$^{Sc}$. Therefore, blocking the action of these endogenous antibodies may slow the disease progression or have other beneficial effects. The YYR-specific monoclonal antibodies may be used as substrates to raise another set of monoclonal antibodies reactive to the binding site of the YYR-specific antibodies. These second set of antibodies are known as anti-idiotypic. The anti-idiotype antibodies are useful to neutralize the circulating PrP$^{Sc}$ reactive antibodies.

An anti-prion therapeutic according to the invention may be administered with a pharmaceutically-acceptable diluent, carrier, or excipient, in unit dosage form. For example, conventional pharmaceutical practice may be employed to provide suitable formulations or compositions to administer such anti-prion therapeutics to animals suffering from or presymptomatic for a prion disease, or at risk for developing a prion disease. Any appropriate route of administration can be employed, for example, parenteral, intravenous, subcutaneous, intramuscular, intracranial, intraorbital, ophthalmic, intraventricular, intracapsular, intraspinal, intracisternal, intraperitoneal, intranasal, aerosol, or oral administration.

Methods well known in the art for making formulations are found in, for example, "Remington's Pharmaceutical Sciences." Formulations for parenteral administration can, for example, contain excipients, sterile water, or saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers can be used to control the release of the compounds. Other potentially useful parenteral delivery systems for anti-prion therapeutic compounds include ethylene-vinyl acetate copolymer particles, osmotic pumps, implantable infusion systems, and liposomes. Formulations for inhalation can contain excipients, for example, lactose, or can be aqueous solutions containing, for example, polyoxyethylene-9-lauryl ether, glycocholate and deoxycholate, or can be oily solutions for administration in the form of nasal drops, or as a gel.

The methods of the present invention may be used to reduce or prevent the disorders described herein in any animal, for example, humans, domestic pets, or livestock. Where a non-human animal is treated, the anti-prion therapeutic employed is preferably specific for that species.

All publications and patent applications mentioned in this specification are herein incorporated by reference to the same extent as if each independent publication or patent application was specifically and individually to be incorporated by reference.

Other embodiments are within the scope of the following claims.

What is claimed is:

1. An antibody or fragment thereof that binds with high binding affinity to a YYX epitope of a mammalian PrP$^{Sc}$.

2. The antibody of claim 1, wherein said antibody does not specifically bind PrP$^{C}$.

3. The antibody of claim 1, wherein said antibody binds to a YYR epitope of a mammalian PrP$^{Sc}$.

4. The antibody of claim 1, wherein said antibody is a polyclonal antibody generated against a YYR epitope of PrP$^{Sc}$.

5. The antibody of claim 4, wherein said YYX epitope is part of CYYR (SEQ ID NO: 32).

6. The antibody of claim 1, wherein said antibody is a monoclonal antibody generated against a YYR epitope of PrP$^{Sc}$.

7. The antibody of claim 6, wherein said YYR epitope is part of CYYRRYYRYY (SEQ ID NO: 33).

8. The antibody of claim 1, wherein said antibody is an IgG, IgM, IgE, IgD, or IgA.

9. The antibody of claim 1, wherein said antibody fragment is a Fab or Fv fragment.

10. A hybridoma cell line that produces a monoclonal antibody that binds with high binding affinity to a YYX epitope of a mammalian $PrP^{Sc}$.

11. The hybridoma of claim 10, wherein said antibody does not specifically bind $PrP^{C}$.

12. The hybridoma cell line of claim 10, wherein said antibody binds to a YYR epitope of a mammalian $PrP^{Sc}$.

13. The hybridoma cell line of claim 12, wherein said YYR epitope is part of CYYRRYYRYY (SEQ ID NO: 33).

14. A composition comprising the antibody of claim 1.

15. The composition of claim 14, wherein said composition further comprises a carrier.

16. The composition of claim 14, wherein said composition is a therapeutic composition.

17. An immunological test kit comprising the antibody of claim 1 and a means for detecting said antibody.

18. A method for detecting $PrP^{Sc}$ in a biological sample, said method comprising the steps of:

(a) contacting said biological sample with the antibody of claim 1 under conditions that allow for complex formation between said antibody and $PrP^{Sc}$; and (b) detecting said complexes as an indication that $PrP^{Sc}$ is present in said biological sample.

19. The method of claim 18, wherein said antibody does not specifically bind $PrP^{C}$.

20. The method of claim 18, wherein said antibody is a polyclonal antibody or fragment thereof.

21. The method of claim 18, wherein said antibody is a monoclonal antibody or fragment thereof.

22. The method of claim 18, wherein said biological sample comprises a tissue or cell, a tissue or cell extract, a bodily fluid, or a biopsy.

23. The method of claim 18, wherein said $PrP^{Sc}$ is from a human, a livestock species, or a pet species.

24. The method of claim 18, wherein said complex is detected using an ELISA, RIA, western blotting, immunoprecipitation, or flow cytometry.

25. The antibody of claim 1, wherein said antibody selectively binds $PrP^{Sc}$ as compared to $PrP^{C}$.

26. The hybridoma of claim 10, wherein said antibody selectively binds $PrP^{Sc}$ as compared to $PrP^{C}$.

* * * * *

UNITED STATES PATENT AND TRADEMARK OFFICE
CERTIFICATE OF CORRECTION

PATENT NO. : 7,041,807 B1  Page 1 of 1
APPLICATION NO. : 09/602775
DATED : May 9, 2006
INVENTOR(S) : Neil Cashman et al.

It is certified that error appears in the above-identified patent and that said Letters Patent is hereby corrected as shown below:

On the Cover Page item [56], in References Cited, in OTHER PUBLICATIONS,
    Page 2, in "Coulthart and Cashman", replace "pubilc" with --public--; and
    Page 3, in "Field", replace "Infecions" with --infections--; and
    Page 3, in "Schaller et al.", replace "Encephatophathy" with --Encelphalopathy--;
    and
    Page 4, in "Kurschner et al.", replace "Prion Protein (PrP) selctively" with --Prion Protein (PrP) selectively--; and
    Page 4, in "Oesch et al.", replace "Scraple Prion Protein" with --Scrapie Prion Protein--.

Column 8, Line 57, replace "labelled" with --labeled--.

Column 9, Line 9, replace "immunblotting" with --immunoblotting--.

Column 17, Line 19, replace "supernantants" with --supernatants--.

Column 18
    Line 51, replace "Ten µl" with --10 µl--; and
    Line 66, replace "bromphenol" with --bromophenol--.

Column 22, Line 35, replace "diagnotic" with --diagnostic--.

Column 23, Line 33, replace "immunoreativity" with --immunoreactivity--.

Signed and Sealed this

Sixth Day of March, 2007

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 7,041,807 B1 | Page 1 of 1 |
| APPLICATION NO. | : 09/602775 | |
| DATED | : May 9, 2006 | |
| INVENTOR(S) | : Neil Cashman et al. | |

It is certified that error appears in the above-identified patent and that said Letters Patent is hereby corrected as shown below:

Column 24, Line 12, replace "eosinophiles" with --eosinophils--.

Signed and Sealed this

Twenty-ninth Day of May, 2007

JON W. DUDAS
*Director of the United States Patent and Trademark Office*

UNITED STATES PATENT AND TRADEMARK OFFICE
CERTIFICATE OF CORRECTION

PATENT NO. : 7,041,807 B1
APPLICATION NO. : 09/602775
DATED : May 9, 2006
INVENTOR(S) : Cashman et al.

It is certified that error appears in the above-identified patent and that said Letters Patent is hereby corrected as shown below:

On the Title Page

Item [*] Notice: Subject to any disclaimer, the term of this patent is extended or adjusted under 35 USC 154(b) by 342 days Delete the phrase "by 342 days" and insert --by 404 days--

Signed and Sealed this

Nineteenth Day of February, 2008

JON W. DUDAS
*Director of the United States Patent and Trademark Office*